(12) United States Patent
Lange et al.

(10) Patent No.: US 11,344,512 B2
(45) Date of Patent: May 31, 2022

(54) TITRATION OF TAPENTADOL

(71) Applicant: Grünenthal GmbH, Aachen (DE)

(72) Inventors: Claudia Lange, Wiesloh (DE);
Ferdinand Rombout, NL-Klimmen (NL)

(73) Assignee: Grünenthal GmbH, Aachen (DE)

( * ) Notice: Subject to any disclaimer, the term of this patent is extended or adjusted under 35 U.S.C. 154(b) by 0 days.

(21) Appl. No.: 16/439,135

(22) Filed: Jun. 12, 2019

(65) Prior Publication Data
US 2019/0290603 A1 Sep. 26, 2019

Related U.S. Application Data

(63) Continuation of application No. 15/369,257, filed on Dec. 5, 2016, now abandoned, which is a continuation of application No. 14/945,289, filed on Nov. 18, 2015, now abandoned, which is a continuation of application No. 12/106,695, filed on Apr. 21, 2008, now abandoned.

(60) Provisional application No. 60/907,939, filed on Apr. 23, 2007.

(30) Foreign Application Priority Data

Apr. 23, 2007 (EP) .................... 07008218

(51) Int. Cl.
*A61K 31/135* (2006.01)
*A61K 31/137* (2006.01)
*A61K 9/00* (2006.01)

(52) U.S. Cl.
CPC .......... *A61K 31/137* (2013.01); *A61K 9/0053* (2013.01)

(58) Field of Classification Search
CPC ............................ A61K 31/137; A61K 9/0053
See application file for complete search history.

(56) References Cited

U.S. PATENT DOCUMENTS

| | | | |
|---|---|---|---|
| 4,612,008 | A | 9/1986 | Wong et al. |
| 4,765,989 | A | 8/1988 | Wong et al. |
| 4,783,337 | A | 11/1988 | Wong et al. |
| 6,248,737 | B1 | 6/2001 | Buschmann et al. |
| 6,339,105 | B1 | 1/2002 | Kamin et al. |
| 6,344,558 | B1 | 2/2002 | Buschmann et al. |
| 6,605,644 | B2 | 8/2003 | Kamin et al. |
| 2002/0010178 | A1 | 1/2002 | Buschmann et al. |
| 2004/0126416 | A1 | 7/2004 | Reidenberg et al. |
| 2004/0259956 | A1 | 12/2004 | Wright et al. |
| 2005/0058706 | A1 | 3/2005 | Bartholomaeus et al. |
| 2009/0005458 | A1 | 1/2009 | Rombout et al. |
| 2017/0087103 | A1 | 3/2017 | Bartholomaeus et al. |

FOREIGN PATENT DOCUMENTS

| | | |
|---|---|---|
| CA | 2 464 578 A1 | 5/2003 |
| EP | 0 693 475 A1 | 1/1996 |
| JP | 2006-513184 A | 4/2006 |
| JP | 2006-519849 A | 8/2006 |
| JP | 2010-531296 A | 9/2010 |
| KR | 10-2004-0047964 A | 6/2004 |
| MX | 2009011346 A | 11/2009 |
| RU | 2 150 465 C1 | 6/2000 |
| WO | 03/035053 A1 | 5/2003 |
| WO | 2004/054553 A1 | 7/2004 |
| WO | 2004/080447 A1 | 9/2004 |
| WO | 2008/128740 A1 | 10/2008 |

OTHER PUBLICATIONS

ClinicalTrials.gov—History of Changes for Study_NCT00421928—Apr. 1, 2007.
ClinicalTrials.gov—History of Changes for Study_NCT00449176—Mar. 16, 2007.
ClinicalTrials.gov—History of Changes for Study_NCT00361504—Apr. 1, 2007.
Johnson & Johnson, "A Study to Evaluate Long-Term Safety of Multiple Doses of Tapentadol (CG5503) Prolonged-Release (PR) and Oxycodone Controlled-Release (CR) in Patients With Chronic Pain", www.clinicaltrials.gov/ct2/show/study/NCT00361504?term=tapentdaol&rank=12, Apr. 2, 2007.
European Search Report dated Jan. 18, 2017 (twelve pages).
English translation of Johnson & Johnson, "A Study to Evaluate Long-Term Safety of Multiple Doses of Tapentadol (CG5503) Prolonged-Release (PR) and Oxycodone Controlled-Release (CR) in Patients With Chronic Pain", www-clinicaltrials.gov/ct2/show/study/NCT00361504?term=tapentdaol&rank=12, Apr. 2, 2007.) www.clinicaltrials.gov.
Mutschler et al., "Lehrbuch der Pharmakologie und Toxikologie", Mutschler Arzneimittelwirkungen, 2001, pp. 214-217 (six pages).
Fields, "Summary of Safety Results and Conclusions", NDA 22-304, Tapentadol HCl Clinical Review, Sep. 18, 2009, 122 pages.
"Principles of Opioid Management", Hospice Palliative Care Program, Symptom Guidelines, 2006, 45 pages.
"The Science and Practice of Pharmacy", Remington, 2000, pp. 995-997 (four pages total), 20th Edition.
"Exposure-Response Relationships—Study Design, Data Analysis, and Regulatory Applications", Guidance for Industry, US FDA (Food and Drug Administration), Apr. 2003, pp. 1-25 (28 pages total).
English language translation of Office Action dated May 31, 2017, and issued in connection with Japanese Patent Application No. 2016-009738 (5 pages).
"Symptom Management in Cancer Patients", 2006, pp. 63-66, vol. 17, No. 1.
English translation of Mutschler et al. "Mutschler's Drug Effects," Textbook of Pharmacology and Toxicology, 8th Edition, Stuttgart 2001) (seven pages).
S. Mercadante et al., "Opioid-induced or Pain Relief-Reduced Symptoms in Advanced Cancer Patients", European Journal of Pain, 2006, pp. 153-159, vol. 10.

(Continued)

*Primary Examiner* — Shobha Kantamneni
(74) *Attorney, Agent, or Firm* — Norris McLaughlin, P.A.

(57) ABSTRACT

The use of tapentadol for the manufacture of a medicament comprising at least one administration unit A containing dose a of tapentadol and at least one administration unit B containing dose b of tapentadol, where dose a<dose b, for the treatment of pain.

3 Claims, 12 Drawing Sheets

(56) References Cited

OTHER PUBLICATIONS

U.S. Department of Health and Human Services, "Exposure-Response Relationships—Study, Design, Data Analysis, and Regulatory Applications," Guidance for Industry, Apr. 2003, Food and Drug Administration (twenty-eight pages).
Professor Dr. med. Dr. rer. Nat. Drs. H.c. E. Mutschler et al., "Mutschler Arzneimittelwirkungen—Lehrbuch der Pharmakologie and Toxikologie," 2001, pp. 214-217, Wissenschaftliche Verlagsgesellschaft mbH, Stuttgart (six pages).
R. A. Moore et al., "Prevalence of opioid adverse events in chronic non-malignant pain: systematic review of randomised trials of oral opioids," Arthritis Research & Therapy, Jun. 28, 2005, pp. R1046-R1051, vol. 7, No. 5 (six pages).
A Study to Evaluate Long-Term Safety of Multiple Doses of Tapentadol (CG5503) Prolonged-Release (PR) and Oxycodone Controlled-Release (CR) in Patients With Chronic Pain, History of NCT00361504, https://clinicaltrials.gov/archive/NCTE00361504 (five pages).
Third-party communication submitted Apr. 12, 2017, in connection with European Patent Application No. 16192734.8 (seven pages).
Third-party communication submitted Apr. 18, 2017, in connection with European Patent Application No. 08749016.5 dated (nine pages).
T. M. Tzschentke, et al., "Tapentadol Hydrochloride", Drugs of the Future, 2006, pp. 1053-1061, vol. 31, No. 12.
Louis J. Ravin, Ph.D., "Preformulation", Chapter 76, pp. 1409-1423.
Anthony R. Disanto, Ph.D., "Bioavailability and Bioequivalency", Chapter 77, pp. 1424-1431.
Adelbert M. Knevel, Ph.D., "Separation", Chapter 78, pp. 1432-1442.
G. Briggs Phillips, Ph.D., "Sterilization", Chapter 79, pp. 1443-1454.
Frederick P. Siegel, Ph.D., "Tonicity, Osmoticity, Osmolality, and Osmolarity", Chapter 80, pp. 1455-1472.
Robert L. Giles, BA, et al., "Plastic Packaging Materials", Chapter 81, pp. 1473-1477.
Carl J. Lintner, Ph.D., "Stability of Pharmaceutical Products", Chapter 82, pp. 1478-1486.
Clyde R. Erskine, JR., "Quality Assurance and Control", Chapter 83, pp. 1487-1491.
J. G. Nairn, Ph.D., "Solutions, Emulsions, Suspensions and Extractives", Chapter 84, pp. 1492-1517.
Kenneth E. Avis, DSC, "Parenteral Preparations", Chapter 85, pp. 1518-1541.
Salvatore J. Turco, PharmD., et al., "Intravenous Admixtures", Chapter 86, pp. 1542-1552.
John D. Mullins, Ph.D. "Ophthalmic Preparations", Chapter 87, pp. 1553-1566.
Lawrence H. Block, Ph.D., "Medicated Applications", Chapter 88, pp. 1567-1584.
Edward G. Ripple, Ph.D., "Powders", Chapter 89, pp. 1585-1602.
Robert E. King, Ph.D., et al., "Oral Solid Dosage Forms", Chapter 90, pp. 1603-1632.
Stuart C. Porter, Ph.D., "Coating of Pharmaceutical Dosage Forms", Chapter 91, pp. 1633-1643.
Mark A. Longer, et al., "Sustained-Release Drug Delivery Systems", Chapter 92, pp. 1644-1661.
John J. Sciarra, Ph.D., et al., "Aerosols", Chapter 93, pp. 1662-1677.
William E. Evans, et al., "Pharmacogenomics: Translating Functional Genomics into Rational Therapeutics", Oct. 15, 1999, pp. 486-491, vol. 286, Science AAAS.
R. Kleinert, et. al., "(773) Efficacy of a Single Dose of Tapentadol HCl for Analgesia After Third Molar Surgery", p. S44, Abstracts.
Gary E. Ruoff, M.D., "Slowing the Initial Titration Rate Tramadol Improves Tolerability", Phamacotherapy, 1999, p. 88-93, vol. 19, No. 1, Clinical Research Articles.
H. Weber, et al., (312/776) "Efficacy and Safety of Tapentadol HCl in patients with Pain after Bunionectomy", p. S3, Abstracts (2006).
International Search Report dated Aug. 6, 2008 and PCT/ISA/237 Form (Twelve pages).
Bral, 2006 (two pages).
Ivanova, 1991, 135 (two pages).
"Package Leaflet: Information for the User, Zydol® SR 100 mg, 150 mg and 200 mg prolonged release tablets," Royal National Institute of the Blind, 2011, pp. 1-2.
Fields, Ellen, M.D., M.P.H., "NDA 22-304, Tapentadol HCL Clinical Review," 7 Integrated Review of Safety, Sep. 18, 2009, 122 pages.
Document dated Jan. 24, 2014, from Opposition of European Patent No. 2 148 670 B1 (twenty-one pages).
File history of European Patent No. 2 148 670 B1 from Oct. 30, 2008, to Apr. 9, 2014 (eight hundred and thirty-seven pages).
Malinowski, Henry J., "Bioavailability and Bioequivalence Testing", Remington—The Science and Practice of Pharmacy, 20th Edition, 2000, four pages.
McQuay, H.J., "Opioids in Chronic Pain", Br. J. Anaesth (1989), vol. 63, pp. 213-226.
FraserHealth, "Principles of Opioid Management—Symptom Guidelines", Nov. 24, 2006, pp. 1-45.
Grounds for Appeal dated May 30, 2014 (fifty-one pages).
R.M. Langford et al., British Journal of Pain, 2016, vol. 10(4), 217-221 ("Langford et al.").
Fachinformation Palexia® retard (2020) ("Palexia®").
Highlights of Prescribing Information NUCYNTA® ER (2016) ("NUCYNTA®").
M.J. Sánchez del Águila et al., Clinical Therapeutics, 2015, vol. 37(1), 94-113 ("Sánchez del Águila et al.").
Decision dated May 31, 2018, in connection with European Patent No. 2 148 670 B1.
Response dated Jul. 31, 2020, in connection with European Patent Application No. 19 189 638.0.

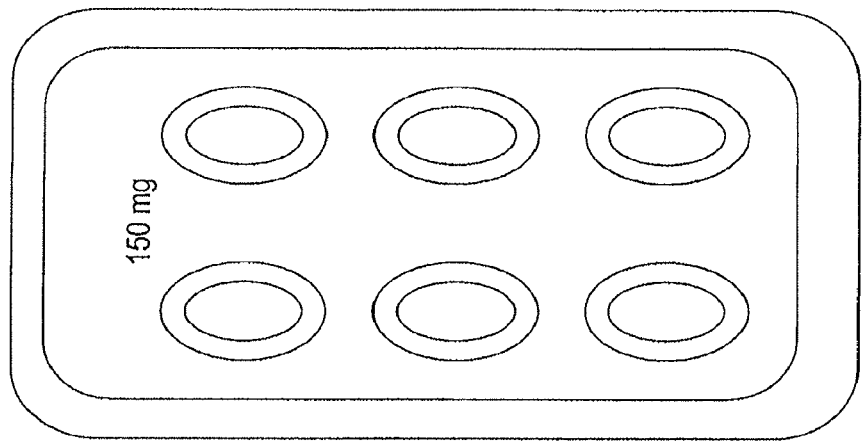
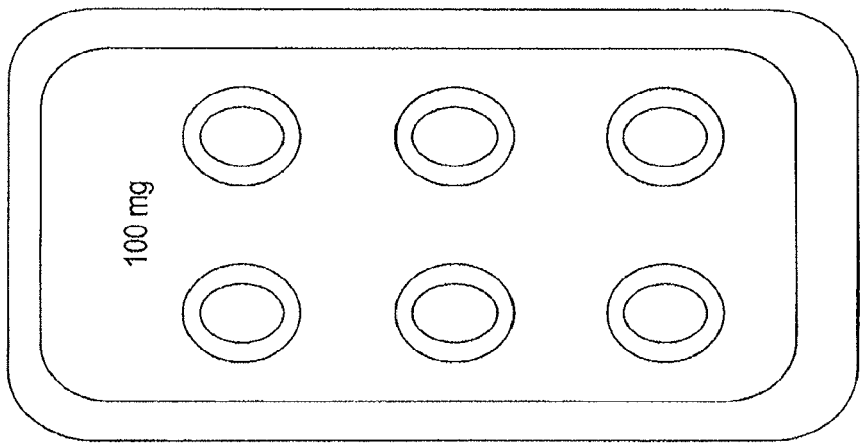
Figure 1
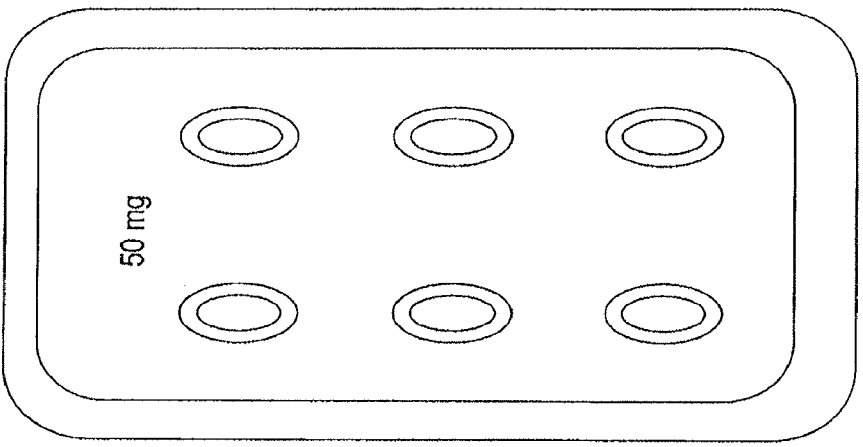

TITRATION OF TAPENTADOL

CROSS REFERENCE TO RELATED APPLICATIONS

This application is a continuation of U.S. patent application Ser. No. 15/369,257, filed Dec. 5, 2016, which is a continuation of U.S. patent application Ser. No. 14/945,289, filed Nov. 18, 2015, now abandoned, which is a continuation of U.S. patent application Ser. No. 12/106,695, filed Apr. 21, 2008, now abandoned, which: (i) claims the benefit of U.S. Provisional Patent Application No. 60/907,939, filed Apr. 23, 2007; and (ii) claims foreign priority benefit under 35 U.S.C. § 119 of European Patent Application No. 07 008 218.5, filed Apr. 23, 2007, the entire contents of each of which are incorporated herein by reference.

FIELD OF THE INVENTION

The present invention relates to a dosing regimen for the administration of the analgesic tapentadol, preferably as a prolonged release dosage form. The dosing regimen achieves the desired analgesic effect while reducing or delaying the onset of side effects.

BACKGROUND OF THE INVENTION

Tapentadol (CG5503), the chemical name for which is (−)-(1R,2R)-3-(3-dimethylamino-1-ethyl-2-methyl-propyl)-phenol, is a synthetic, centrally-acting analgesic that is effective for the treatment of moderate to moderately-severe acute or chronic pain. The compound can be employed as the free base or its pharmaceutically acceptable salts and solvates. Preparation of the free base is known from EP-A 693 475.

Patients experiencing acute or chronic pain require an analgesic therapeutic regimen that is both effective and well tolerated. The two traditional categories of analgesics, i.e. opioids and nonsteroidal anti-inflammatory drugs (NSAIDs), are both effective but are associated with potentially serious side effects. Concerns regarding tolerance and dependence minimize the use of narcotics such as morphine and codeine for the treatment of acute or chronic pain. Patients on chronic NSAID therapy risk severe gastrointestinal symptoms, including ulceration and bleeding which have been estimated to result in up to 20,000 deaths each year.

An alternative to this dilemma is tapentadol, a non-NSAID analgesic which is indicated for the management of moderate to severe pain.

Tapentadol is an investigational, centrally acting analgesic with a dual mode of action consisting of μ-opioid receptor (MOR) agonism and norepinephrine (NE) reuptake inhibition. The efficacy, safety, and pharmacokinetic profile of tapentadol indicate that the drug may be useful in treating acute as well as chronic pain.

The activity of tapentadol is independent of metabolic activation and resides in a single enantiomer which readily crosses the blood-brain barrier; hence, tapentadol displays a rapid onset of action after administration. The biotransformation of tapentadol by metabolic enzymes results in deactivation, i.e., tapentadol has no active metabolites, and the main metabolic pathway for elimination is phase II glucuronidation. Phase I biotransformations such as hydroxylation and N-demethylation play only a minor role in the metabolic fate of tapentadol. Owing to the minor involvement of phase I metabolic pathways, tapentadol has a low potential for drug-drug interactions and interindividual variability (cf. Tzschentke T. M. et al. Tapentadol Hydrochloride. *Drugs of the Future* 2006, 31, 1053-1061; Evans W. E., Relling, M. V. Pharmacogenomics: Translating Functional Genomics into Rational Therapies. *Science* 1999, 286, 487-491).

Tapentadol is well tolerated, however, nuisance adverse events such as somnolence can occur, e.g., during the initiation of treatment, which may lead to early discontinuation of the treatment. The most frequently reported adverse events observed in clinical trials of tapentadol are associated with the central nervous system (e.g. somnolence, dizziness/vertigo, headache) and the gastrointestinal tract (e.g. constipation, nausea, vomiting) (cf. Weber H. et al. *Journal of Pain* 2006, 7, S3; Kleinert R. et al. *Journal of Pain* 2006, 7, 44).

The occurrence of somnolence is of particular concern, because drug-induced somnolence may have a negative effect on activities of daily living and impair the physical functioning of chronic pain patients. "Quality of Life" may suffer thereby.

Various concepts to decrease the occurrence of adverse side effects are known in the prior art. For example, eating and drinking habits, drug formulations, and/or the route of administration can be changed. Further, a second drug can be co-administered simultaneously with, before or after the drug of interest in order to suppress its adverse side-effects. However, these actions can impair patient compliance by, for example, forcing the patient to change his habitual life style. Further, changing the mode of administration, e.g. from oral to rectal, is conceived by many patients as uncomfortable and unhygienic. The resulting decreased patient compliance can result in termination of a required drug therapy.

SUMMARY OF THE INVENTION

It is an object of the present invention to improve the tolerability of tapentadol in the treatment of pain, preferably of chronic pain, particularly to reduce the frequency of somnolence; one of the most frequently reported adverse events, as well other adverse events, without diminishing the efficacy of the compound and the patient compliance.

These and other objects have been achieved by the invention as described and claimed hereinafter.

The present invention relates to the use of tapentadol for the manufacture of a medicament comprising
at least one administration unit A containing dose a of tapentadol and
at least one administration unit B containing dose b of tapentadol,
where dose a<dose b,
for the treatment of pain.

Preferably, tapentadol is used for the manufacture of a medicament, where dose a of tapentadol is administered during a first administration interval and dose b of tapentadol is administered during a second administration interval following said first administration interval, where dose a<dose b, for the treatment of pain.

It has been surprisingly found that the tolerability of tapentadol may be improved by initiating the treatment at a comparatively low dose of tapentadol and successively increasing the dose according to a titration regimen.

BRIEF DESCRIPTION OF THE DRAWINGS

FIGS. 1, 2, 3 and 4 show preferred embodiments of the medicament according to the invention in form of blister packages.

DETAILED DESCRIPTION OF THE INVENTION

Definitions

Figure 2:
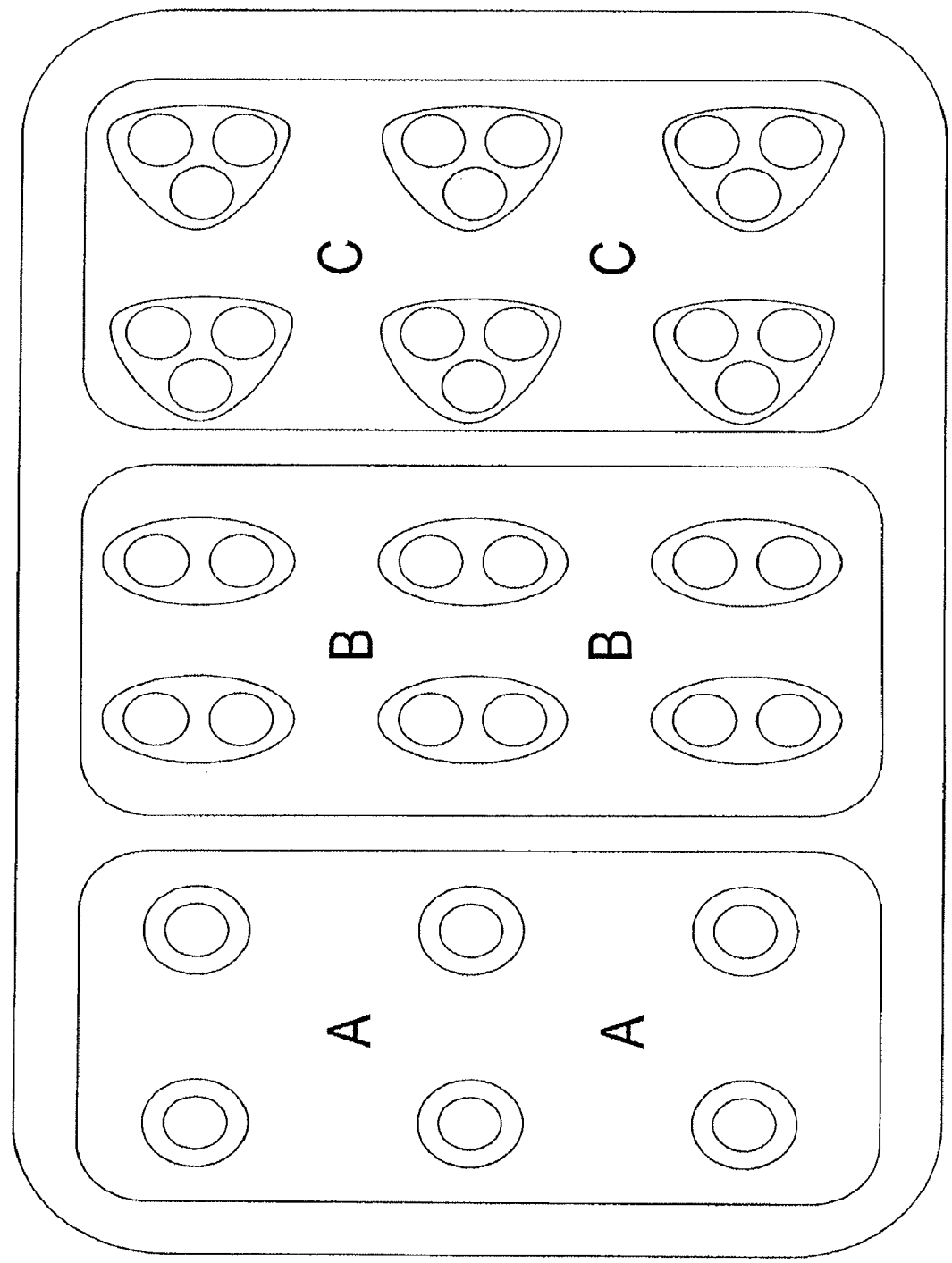

As used hereinafter, the word "tapentadol" is intended to include (−)-(1R,2R)-3-(3-dimethylamino-1-ethyl-2-methylpropyl)-phenol, its pharmaceutically acceptable salts and solvates thereof. Suitable pharmaceutically acceptable salts include salts of inorganic acids, such as hydrochloric acid (tapentadol HCl), hydrobromic acid and sulfuric acid, and salts of organic acids, such as methane sulfonic acid, fumaric acid, maleic acid, acetic acid, oxalic acid, succinic acid, malic acid, tartaric acid, mandelic acid, lactic acid, citric acid, glutamic acid, acetylsalicylic acid, nicotinic acid, aminobenoic acid, α-liponic acid, hippuric acid and asparaginic acid. The preferred salt is the hydrochloride salt.

For the purpose of the specification, doses of tapentadol relate to the free base. Thus, when a pharmaceutically acceptable salt is used instead, its dose has to be adapted to the equivalent dose of the free base. For example, a dose of "200 mg" means an amount of 200 mg of the free base or any equivalent amount of a pharmaceutically acceptable salt or solvate corresponding to 200 mg of the free base (e.g. about 233 mg of the hydrochloride). If not expressly stated otherwise, doses are "per administration", not "per day".

Use of Tapentadol for the Manufacture of a Medicament for Treating Pain

Tapentadol is indicated for the treatment of moderate to severe acute and chronic pain. Clinical studies have shown tapentadol prolonged release (PR) to be an effective treatment for chronic joint pain (osteoarthritis of the hip or knee) and low back pain. There is also indication that tapentadol prolonged release (PR) is useful for the treatment of chronic cancer pain and chronic painful diabetic peripheral neuropathy (DPN). Further, clinical studies revealed that tapentadol immediate release (IR) is useful in the treatment of acute dental pain, acute pain after bunionectomy and acute pain after abdominal surgery. Further, ongoing studies are concerned with acute pain after hip replacement, acute pain after abdominal hysterectomy (visceral pain) and acute pain in patients waiting for joint replacement.

Tapentadol is well tolerated, however, nuisance adverse events can occur during initiation of treatment with tapentadol. These side effects may lead to early discontinuation of tapentadol therapy.

Titration of a therapeutic agent is sometimes used by practicing clinicians to minimize adverse events associated with centrally-acting agents such as antidepressants and anticonvulsants. Although titration may minimize the adverse side effects associated with a particular agent, it may also delay the onset of the effect of the agent as well.

For example, the slow titration of the drug tramadol has been reported to reduce the frequency of certain adverse effects such as dizziness, nausea and vomiting (Ruoff G. E., Slowing the Initial Titration Rate of Tramadol Improves Tolerability. *Pharmacotherapy* 1999, 19, 88-93). However, this study also showed that the frequency of somnolence was not significantly reduced by the slow titration of tramadol. This specific pharmacological behavior of tramadol is likely based on its unique properties, particularly its racemic nature, its activating metabolic pathway and number of active metabolites, the change of the relative contribution of the individual metabolites to the overall efficacy of the drug over time, its 5-HT reuptake inhibiting mechanism of action, and the like. The results of Ruoff et al. support the notion that it remains unpredictable whether adverse events in general might be affected by titration of drugs, let alone whether a particular adverse event might be affected.

It has now been discovered that initiating tapentadol therapy according to a titration regimen minimizes adverse side effects associated with tapentadol, particularly somnolence, while maintaining its therapeutic effectiveness which results in a greater tolerability of the drug during therapy.

It has been surprisingly found that particularly adverse events that are associated with the central nervous system, such as somnolence, can be minimized by titration according to the invention. As far as adverse events associated with the gastrointestinal tract are concerned, titration of tapentadol according the present invention is also advantageous.

Furthermore, it has been surprisingly found that at the end of a long term dosing regimen, the occurrence of mild-moderate withdrawal symptoms following drug discontinuation are significantly fewer compared to other opioids, such as oxycodone. Thus, there is little indication of the need for drug tapering (downward titration) at the end of the overall dosing regimen.

A first aspect of the invention relates to the use of tapentadol for the manufacture of a medicament comprising:

at least one administration unit A containing dose a of tapentadol and at least one administration unit B containing dose b of tapentadol, where dose a<dose b, for the treatment of pain, preferably of chronic pain.

As used herein, an "administration unit" may be composed of a single dosage form or of a group of dosage forms. In other words, administration unit X comprises $n_X$ dosage forms, where $n_X$ is an integer≥1.

When $n_X=1$, administration unit X comprises a single dosage form. When $n_X>1$, administration unit X comprises a group of dosage forms which are adapted and intended to be administered simultaneously. In this context, "simultaneously" does not mean exactly at the same time, but approximately at the same time, e.g., within a period of up to five minutes, preferably up to one minute. For example, an administration unit containing 200 mg of tapentadol may be either a single dosage form ($n_X=1$) containing the entire amount of tapentadol (200 mg) or a group of dosage forms ($n_X>1$), e.g., two dosage forms ($n_X=2$) each containing 100 mg of tapentadol; or, e.g., three dosage forms ($n_X=3$) two of which contain 50 mg of tapentadol each and one of which contains 100 mg of tapentadol; or, e.g., four dosage forms ($n_X=4$) each containing 50 mg of tapentadol.

Thus, administration of dose x of tapentadol may be achieved either by administering administration unit X composed of a single dosage form containing dose x of tapentadol or by administering administration unit X composed of a group of $n_X$ dosage forms (with $n_X>1$), the entirety of said group of $n_X$ dosage forms containing dose x of tapentadol, which group of $n_X$ dosage forms is adapted and intended to be administered simultaneously.

Preferably, the invention relates to the use of tapentadol for the manufacture of a medicament comprising
- at least one administration unit A, that is composed of $n_A$ dosage forms the entirety of which contains dose a of tapentadol, and
- at least one administration unit B that is composed of $n_B$ dosage forms the entirety of which contains dose b of tapentadol,
where
  dose a<dose b, and
  $n_A$ and $n_B$ are independently of one another an integer≥1, for the treatment of pain. Preferably $n_A=n_B$, $n_A>n_B$ or $n_A<n_B$.

Preferably, administration unit A and administration unit B are solid.

In one preferred embodiment, tapentadol is used for the manufacture of a medicament, where dose a of tapentadol is administered during a first administration interval of at least one day and dose b of tapentadol is administered during a second administration interval of at least one day following said first administration interval, where dose a<dose b, for the treatment of pain, preferably of chronic pain.

Preferably, dose a is within the range of from 10 to 90 wt.-% of dose b, more preferably from 20 to 80 wt.-%, still more preferably from 45 to 70 wt.-%.

In one preferred embodiment dose a is below the pharmaceutically effective pain treating dose of tapentadol. The pharmaceutically effective pain treating dose of tapentadol may vary individually and can be determined by routine experimentation for a given subject. Usually, the minimum pharmaceutically effective pain treating dose will be above 50 mg twice daily (bid). Preferably, effective pain treatment is to be regarded as at least 5% decrease in pain in an individual, more preferably at least 10%, still more preferably at least 15% and most preferably at least 20% decrease in pain in an individual, taking into account that low serum concentrations of tapentadol suffice to show an effect in individuals that are relatively sensitive and higher serum concentrations of tapentadol are needed to show an effect in persons that are relatively unsensitive. Preliminary clinical trials revealed that a significant pain treating effect is seen at serum concentrations in the range of from about 5 ng/ml (approximately −2 mm visual analog scale (VAS) in a population mean) to about 300 ng/ml (approximately −15 mm visual analog scale (VAS) in a population mean).

Preferably, the ratio of dose a:dose b ([mg]:[mg]) is selected from the group consisting of
(25±5%):(50±5%), (25±5%):(75±5%), (25±5%):(100±5%), (25±5%):(125±5%), (25±5%):(150±5%), (25±5%):(175±5%), (25±5%):(200±5%), (25±5%):(225±5%), (25±5%):(250±5%);
(50±5%):(75±5%), (50±5%):(100±5%), (50±5%):(125±5%), (50±5%):(150±5%), (50±5%):(175±5%), (50±5%):(200±5%), (50±5%):(225±5%), (50±5%):(250±5%);
(75±5%):(100±5%), (75±5%):(125±5%), (75±5%):(150±5%), (75±5%):(175±5%), (75±5%):(200±5%), (75±5%):(225±5%), (75±5%):(250±5%);
(100±5%):(125±5%), (100±5%):(150±5%), (100±5%):(175±5%), (100±5%):(200±5%), (100±5%):(225±5%), (100±5%):(250±5%);
(125±5%):(150±5%), (125±5%):(175±5%), (125±5%):(200±5%), (125±5%):(225±5%), (125±5%):(250±5%);
(150±5%):(175±5%), (150±5%):(200±5%), (150±5%):(225±5%), (150±5%):(250±5%);
(175±5%):(200±5%), (175±5%):(225±5%), (175±5%):(250±5%);
(200±5%):(225±5%), (200±5%):(250±5%); and
(225±5%):(250±5%).

In a preferred embodiment, under in vitro conditions, administration unit A releases 50% of dose a in a shorter or in a longer time interval than administration unit B releases 50% of dose b. The skilled person is fully aware of suitable in vitro conditions, e.g., release may be investigated according to the European Pharmacopoeia, paddle method, 100 Upm, artificial gastric juice.

In one preferred embodiment administration unit A and administration unit B are adapted to be administered via different routes, which preferably are independently selected from the group consisting of orally, buccally, sublingually, transmucosally, intralumbally, intraperitoneally, transdermally, intraveneously, intramusculously, intragluteally, intracutaneously and subcutaneously. Most preferably, however, administration unit A and administration unit B are adapted to be administered via the same route, preferably orally.

In another preferred embodiment, the medicament further comprises at least one administration unit C containing dose c of tapentadol, where dose b<dose c. Preferably, dose a is within the range of from 10 to 65 wt.-% of dose c, more preferably from 20 to 55 wt.-%, and dose b is within the range of from 35 to 90 wt.-% of dose c, more preferably from 45 to 80 wt.-%.

In yet another preferred embodiment, tapentadol is used for the manufacture of a medicament, where dose a of tapentadol is administered during a first administration interval of at least one day, dose b of tapentadol is administered during a second administration interval of at least one day following said first administration interval, and dose c of tapentadol is administered during a third administration interval of at least one day following said second administration interval, where dose a<dose b<dose c, for the treatment of pain, preferably of chronic pain.

Preferably, the ratio of dose a:dose b:dose c ([mg]:[mg]:[mg]) is selected from the group consisting of
(25±5%):(50±5%):(75±5%), (25±5%):(50±5%):(100±5%), (25±5%):(50±5%):(125±5%),
(25±5%):(50±5%):(150±5%), (25±5%):(50±5%):(175±5%), (25±5%):(50±5%):(200±5%),
(25±5%):(50±5%):(225±5%), (25±5%):(50±5%):(250±5%); (25±5%):(75±5%):(100±5%),
(25±5%):(75±5%):(125±5%), (25±5%):(75±5%):(150±5%), (25±5%):(75±5%):(175±5%),
(25±5%):(75±5%):(200±5%), (25±5%):(75±5%):(225±5%), (25±5%):(75±5%):(250±5%);
(25±5%):(100±5%):(125±5%), (25±5%):(100±5%):(150±5%),
(25±5%):(100±5%):(175±5%), (25±5%):(100±5%):(200±5%),
(25±5%):(100±5%):(225±5%), (25±5%):(100±5%):(250±5%);
(25±5%):(125±5%):(150±5%), (25±5%):(125±5%):(175±5%),
(25±5%):(125±5%):(200±5%), (25±5%):(125±5%):(225±5%), (25±5%):(125±5%):(250±5%); (175±5%),
(25±5%):(150±5%):(200±5%), (225±5%),
(25±5%):(150±5%):(250±5%); (200±5%),
(25±5%):(175±5%):(225±5%), (250±5%);
(25±5%):(200±5%):(225±5%), (250±5%);
(25±5%):(225±5%):(250±5%);
(50±5%):(75±5%):(100±5%), (125±5%), (50±5%):(75±5%):(150±5%),
(50±5%):(75±5%):(175±5%), (200±5%), (50±5%):(75±5%):(225±5%),
(50±5%):(75±5%):(250±5%); (125±5%),
(50±5%):(100±5%):(150±5%), (175±5%),
(50±5%):(100±5%):(200±5%), (225±5%),
(50±5%):(100±5%):(250±5%); (150±5%),
(50±5%):(125±5%):(175±5%), (200±5%),
(50±5%):(125±5%):(225±5%), (250±5%);
(50±5%):(150±5%):(175±5%); (200±5%),
(50±5%):(150±5%):(225±5%), (250±5%);
(50±5%):(175±5%):(200±5%), (225±5%),
(50±5%):(175±5%):(250±5%); (225±5%),
(50±5%):(200±5%):(250±5%); (250±5%);
(75±5%):(100±5%):(125±5%), (150±5%),
(75±5%):(100±5%):(175±5%), (200±5%),
(75±5%):(100±5%):(225±5%), (250±5%);
(75±5%):(125±5%):(150±5%), (175±5%),
(75±5%):(125±5%):(200±5%), (225±5%),
(75±5%):(125±5%):(250±5%); (175±5%),
(75±5%):(150±5%):(200±5%), (225±5%),
(75±5%):(150±5%):(250±5%); (200±5%),
(75±5%):(175±5%):(225±5%), (250±5%);
(75±5%):(200±5%):(225±5%), (250±5%);
(75±5%):(225±5%):(250±5%);
(100±5%):(125±5%):(150±5%), (175±5%),
(100±5%):(125±5%):(200±5%), (225±5%),
(100±5%):(125±5%):(250±5%); (175±5%),
(100±5%):(150±5%):(200±5%), (225±5%),
(25±5%):(150±5%): (25±5%):(150±5%):
(25±5%):(175±5%):
(25±5%):(175±5%):
(25±5%):(200±5%):
(50±5%):(75±5%):
(50±5%):(75±5%):
(50±5%):(100±5%):
(50±5%):(100±5%):
(50±5%):(125±5%):
(50±5%):(125±5%):
(50±5%):(150±5%):
(50±5%):(150±5%):
(50±5%):(175±5%):
(50±5%):(200±5%):
(50±5%):(225±5%):
(75±5%):(100±5%):
(75±5%):(100±5%):
(75±5%):(100±5%):
(75±5%):(125±5%):
(75±5%):(125±5%):
(75±5%):(150±5%):
(75±5%):(150±5%):
(75±5%):(175±5%):
(75±5%):(200±5%):
(100±5%):(125±5%):
(100±5%):(125±5%):
(100±5%):(150±5%):
(100±5%):(150±5%):
(100±5%):(150±5%):(250±5%); (200±5%),
(100±5%):(175±5%):(225±5%), (250±5%);
(100±5%):(200±5%):(225±5%), (250±5%);
(100±5%):(225±5%):(250±5%);
(125±5%):(150±5%):(175±5%), (200±5%),
(125±5%):(150±5%):(225±5%), (250±5%);
(125±5%):(175±+5%):(200±5%), (225-5%),
(1255%):(175±5%):(250±5%); (225±5%),
(125±5%):(200±5%):(250±5%); (250±5%);
(150±5%):(175±5%):(200±5%), (225±5%),
(150±5%):(175±5%):(250±5%); (225±5%),
(150±5%):(200±5%):(250±5%); (250±5%);
(175±5%):(200±5%):(225±5%), (250±5%);
(175±5%):(225±5%):(250±5%); and
(200±5%):(225±5%):(250±5%).
(100±5%):(175±5%): (200±5%),
(100±5%):(175±5%): (250±5%);
(100±5%):(200±5%):
(125±5%):(150±5%): (200±5%),
(125±5%):(150±5%):
(125±5%):(175±5%):
(125±5%):(200±5%):
(125±5%):(2255%):
(150±5%):(175±5%):
(150±5%):(200±5%):
(150±5%):(225±5%):
(175±5%):(200±5%):

In a preferred embodiment, the medicament further comprises at least one administration unit D containing dose d of tapentadol, where dose c<dose d.

In a preferred embodiment, tapentadol is used for the manufacture of a medicament, where dose a of tapentadol is administered during a first administration interval of at least one day, dose b of tapentadol is administered during a second administration interval of at least one day following said first administration interval, dose c of tapentadol is administered during a third administration interval of at least one day following said second administration interval, and dose d of tapentadol is administered during a fourth administration interval of at least one day following said third administration interval, where dose a<dose b<dose c<dose d, for the treatment of pain, preferably of chronic pain. Preferably, dose a is within the range of from 10 to 55 wt.-% of dose d, more preferably 15 to 50 wt.-%, dose b is within the range of from 35 to 75 wt.-% of dose d, more preferably 40 to 70 wt.-%, and dose c is within the range of from 60 to 95 wt.-% of dose d, more preferably 65 to 90 wt.-%.

Still more preferably, the medicament further comprises at least one administration unit E containing dose e of tapentadol, where dose d<dose e.

In a preferred embodiment, tapentadol is used for the manufacture of a medicament, where dose a of tapentadol is administered during a first administration interval of at least one day, dose b of tapentadol is administered during a second administration interval of at least one day following said first administration interval, dose c of tapentadol is administered during a third administration interval of at least one day following said second administration interval, dose d of tapentadol is administered during a fourth administration interval of at least one day following said third administration interval, and dose e of tapentadol is administered during a fifth administration interval of at least one day following said fourth administration interval, where dose a<dose b<dose c<dose d<dose e, for the treatment of pain.

Preferably, dose a is within the range of from 10 to 30 wt.-% of dose e, more preferably 15 to 25 wt.-%, dose b is within the range of from 30 to 50 wt.-% of dose e, more preferably 35 to 45 wt.-%, dose c is within the range of from 50 to 70 wt.-% of dose e, more preferably 55 to 65 wt.-%, and dose d is within the range of from 70 to 90 wt.-% of dose e, more preferably 75 to 85 wt.-%.

Preferably, the daily dose of tapentadol is within the range of from 20 to 550 mg, more preferably 30 to 530 mg and most preferably 40 to 520 mg.

In a preferred embodiment, administration unit A, administration unit B, optional administration unit C, optional administration unit D and optional administration unit E are adapted to be administered once daily (sid) each, and dose a, dose b, optional dose c, optional dose d and optional dose e are each independently within the range of from 20 to 550 mg, more preferably 30 to 530 mg and most preferably 40 to 520 mg.

In another preferred embodiment, administration unit A, administration unit B, optional administration unit C, optional administration unit D and optional administration unit E are adapted to be administered twice daily (bid) each, and dose a, dose b, optional dose c, optional dose d and optional dose e are each independently within the range of from 10 to 275 mg, more preferably 15 to 265 mg and most preferably 20 to 260 mg.

In still another preferred embodiment, administration unit A, administration unit B, optional administration unit C, optional administration unit D and optional administration unit E are adapted to be administered thrice daily (tid) each, and dose a, dose b, optional dose c, optional dose d and optional dose e are each independently within the range of from 6 to 180 mg, more preferably 10 to 175 mg and most preferably 13 to 170 mg.

In a preferred embodiment of the medicament according to the invention, administration unit A comprises $n_A$ dosage forms, administration unit B comprises $n_B$ dosage forms, optional administration unit C comprises $n_C$ dosage forms, optional administration unit D comprises $n_D$ dosage forms and optional administration unit E comprises $n_E$ dosage forms, where $n_A=n_B$ or $n_A<n_B$ or $n_A>n_B$. The $n_X$ dosage forms belonging to administration unit X are to be administered simultaneously, i.e. approximately at the same time. Preferably, $n_A<n_B\leq$optional $n_C\leq$optional $n_D\leq$optional $n_E$.

The medicament according to the invention is adapted to administer tapentadol by initiating the treatment at a comparatively low dose of tapentadol (dose a), preferably at a dose of 25 mg±5%, 50 mg±5%, 75 mg±5% or 100 mg±5%, more preferably below the pharmaceutically effective pain treating dose of tapentadol, and successively increasing the dose according to a titration regimen (dose b, optional dose c, optional dose d and optional dose e).

Usually, initial dose a is administered not only once, but several times for several days, preferably twice daily (bid), during a certain period of time (first administration interval), e.g., during three days. Thus, for example, initial dose a is administered on the first day of said first administration interval by means of two administration units A (e.g., one administration unit A is administered in the morning and one administration unit A is administered in the evening of said first day), on the second day of said first administration interval by means of two further administration units A (e.g., one administration unit A is administered in the morning and one administration unit A is administered in the evening of said second day) and on the third day of said first administration interval by means of two further administration units A (e.g., one administration unit A is administered in the morning and one administration unit A is administered in the evening of said third day).

Thus, a total of six administration units A, each containing dose a of tapentadol, is needed in order to administer tapentadol during this exemplified first administration interval.

Thereafter, following the first administration interval, the increase of the dose of tapentadol according to the titration regimen may be realized by administering dose b, e.g., also during a period of three days (second administration interval), e.g., twice daily (bid).

Thus, for example, consecutive dose b is administered on the first day of said second administration interval by means of two administration units B (e.g., one administration unit B is administered in the morning and one administration unit B is administered in the evening of said first day), on the second day of said second administration interval by means of two administration units B (e.g., one administration unit B is administered in the morning and one administration unit B is administered in the evening of said second day) and on the third day of said second administration interval by means of two administration units B (e.g., one administration unit B is administered in the morning and one administration unit B is administered in the evening of said third day).

Thus, a total of six administration units B, each containing dose b of tapentadol, is needed in order to administer tapentadol during this exemplified second administration interval.

Thereafter, following the second administration interval, the further increase of the dose of tapentadol according to the titration regimen may optionally be realized by administering doses c, d and e of tapentadol, i.e. by administering administration units C, D and E during a third, fourth and fifth administration interval, respectively.

Patients may be allowed 1, 2 or more doses of tapentadol, e.g. 25 mg, at least 6 hours apart, as supplemental analgesia.

As administration unit X may comprise $n_X$ dosage forms, two cases may be distinguished:

when $n_X=1$, every administration of administration unit X is performed by administering a single dosage form containing dose x of tapentadol at the respective point in time during the titration regimen;

when $n_X>1$, every administration of administration unit X is performed by simultaneously administering a plurality of dosage forms, namely $n_X$ dosage forms, at the respective point in time during the titration regimen, wherein each of the $n_X$ dosage forms contains tapentadol in an amount below dose x but the entirety of all $n_X$ dosage forms contains dose x of tapentadol. The $n_X$ dosage forms of administration unit X can be identical or different.

When $n_X>1$, the dosage forms belonging to administration unit X may be identical or different and may be provided in the same package or in different packages. For example, if dose x of administration unit X is 250 mg and $n_X$ is 2, the first dosage form may contain 100 mg of tapentadol and the second dosage form may contain 150 mg of tapentadol, or the first dosage form may contain 200 mg of tapentadol and the second dosage form may contain 50 mg of tapentadol, so that the entirety of the 2 dosage forms of administration unit X contains the required dose x of 250 mg of tapentadol. The skilled person recognizes that the $n_X$ dosage forms may be provided in the same package or in different packages. For example, a first dosage form containing 200 mg of tapentadol may be taken from a first package and a second dosage form containing 50 mg of tapentadol may be taken from a second package and both dosage forms may be combined in order to form an administration unit containing a dose of 250 mg of tapentadol.

This embodiment is further illustrated in FIG. 1. For example, administration of an administration unit containing a dose of 150 mg of tapentadol may be realized by administering
- three dosage forms each containing 50 mg of tapentadol (to the left);
- one dosage form containing 50 mg of tapentadol (to the left) and one dosage form containing 100 mg of tapentadol (in the middle); or
- a single dosage form containing 150 mg of tapentadol (to the right).

Preferably, $n_A$, $n_B$, optional $n_C$, optional $n_D$ and optional $n_E$ are independently of one another 1, 2, 3, 4 or 5.

In one preferred embodiment, all dosage forms contained in the medicament according to the invention are different and/or $n_A = n_B =$ optional $n_C =$ optional $n_D =$ optional $n_E = 1$.

In another preferred embodiment, all dosage forms contained in the medicament according to the invention are identical, i.e. contain the same amount of tapentadol, and $n_A < n_B <$ optional $n_C <$ optional $n_D <$ optional $n_E$, more preferably $n_A = 1$, $n_B = 2$, optional $n_C = 3$, optional $n_D = 4$, and optional $n_E = 5$. Preferably, dose $a/n_A =$ dose $b/n_B =$ optional dose $c/n_C =$ optional dose $d/n_D =$ optional dose $e/n_E$.

Preferably, the medicament according to the invention is provided in form of a packaging containing one or more administration units A, one or more administration units B, optionally one or more administration units C, optionally one or more administration units D and optionally one or more administration units E.

For example, the medicament according to the invention may be provided in form of a blister packaging containing 36 identical dosage forms each containing, e.g., 50 mg±5% of tapentadol. When dose a amounts to, e.g., 50 mg±5% of tapentadol, administration units A each comprise a single dosage form ($n_A = 1$). For example, six of the dosage forms in the blister packaging may be marked as administration units A and/or may be locally separated from the other dosage forms in the blister packaging. When dose b amounts to, e.g., 100 mg±5% of tapentadol, administration units B each comprise two dosage forms ($n_B = 2$). For example, twelve of the dosage forms in the blister packaging may be divided into six groups each group comprising two dosage forms. Every group may be marked as administration unit B and/or may be locally separated from the other dosage forms in the blister packaging. When dose c amounts to, e.g., 150 mg±5% of tapentadol, administration units C each comprise three dosage forms ($n_C = 3$). For example, eighteen of the dosage forms in the blister packaging may be divided into six groups each group comprising three dosage forms. Every group may be marked as administration unit C and/or may be locally separated from the other dosage forms in the blister packaging. This embodiment of the medicament according to the invention is further illustrated in FIGS. 2 and 3.

Figure 4:
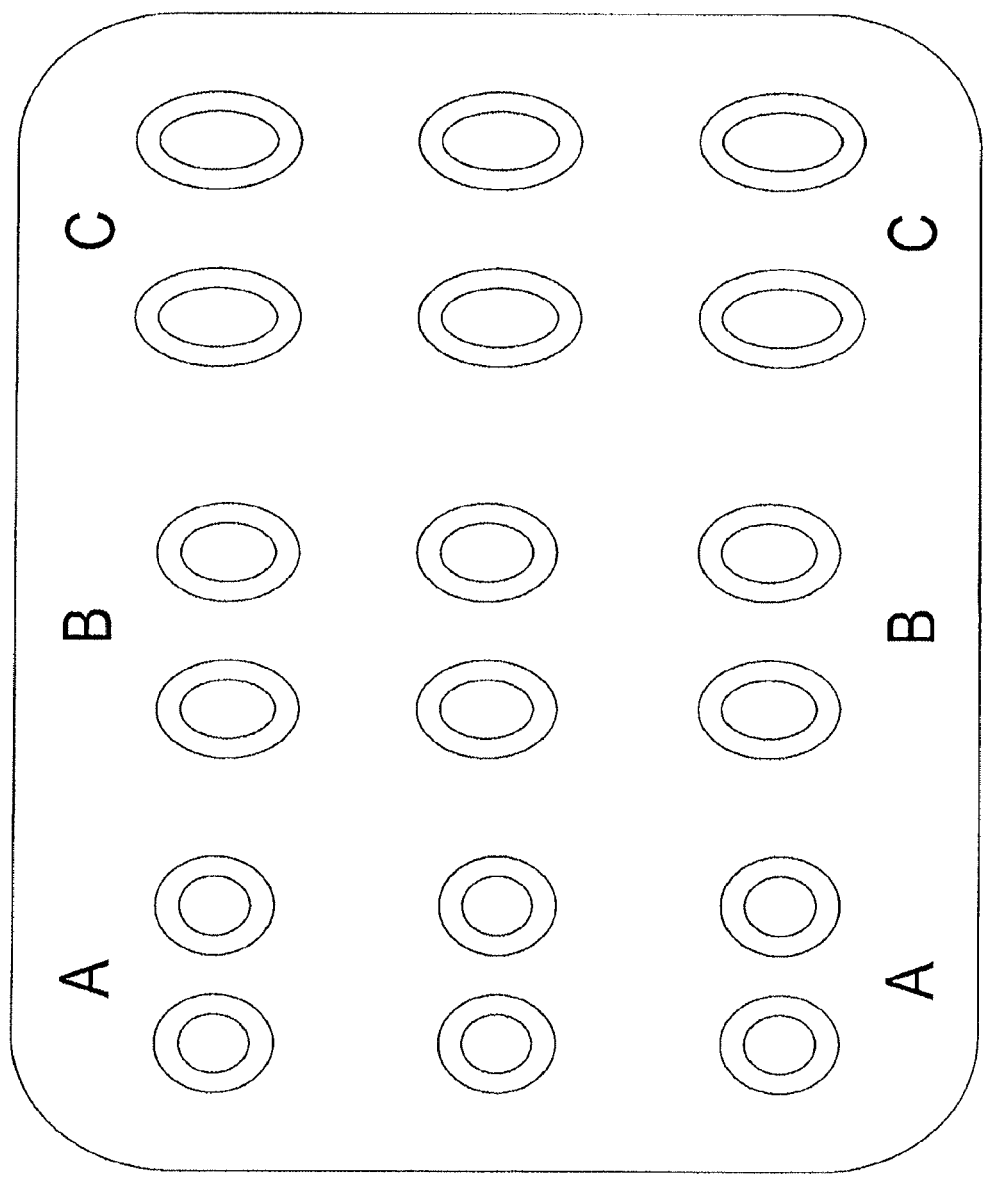

Alternatively, the medicament according to the invention may be provided in form of a blister packaging containing, e.g., 18 administration units each consisting of a single dosage form ($n_X = 1$). These administration units may be divided into three groups each comprising 6 dosage forms. For example, six of the dosage forms in the blister packaging may each contain dose a, e.g., 50 mg±5% of tapentadol, and may be marked as administration units A and/or may be locally separated from the other dosage forms in the blister packaging. Another six of the dosage forms in the blister packaging may each contain dose b, e.g., 100 mg±5% of tapentadol, and may be marked as administration unit B and/or may be locally separated from the other dosage forms in the blister packaging. The remaining six of the dosage forms in the blister packaging may each contain dose c, e.g., 150 mg±5% of tapentadol, and may be marked as administration unit C and/or may be locally separated from the other dosage forms in the blister packaging. This embodiment of the medicament according to the invention is further illustrated in FIG. 4.

Preferably, the medicament according to the invention comprises a plurality of administration units A, a plurality of administration units B, optionally a plurality of administration units C, optionally a plurality of administration units D and optionally a plurality of administration units E. Preferably, these administration units are adapted to be administered sequentially, preferably in alphabetical order. Preferably, the entirety of all administration units A (each comprising $n_A$ dosage forms) is adapted to be administered during a first administration interval and the entirety of all administration units B (each comprising $n_B$ dosage forms) is adapted to be administered during a second administration interval following the first administration interval, i.e. after the administration of the entirety of all administration units A has been completed.

In a preferred embodiment of the present invention, the medicament is provided in form of a packaging comprising a plurality of administration units A, a plurality of administration units B, optionally a plurality of administration units C, optionally a plurality of administration units D and optionally a plurality of administration units E, which are adapted to be administered in sequential, alphabetical order, preferably twice daily (bid), so that all administration units A are adapted to be administered during a first administration interval, all administration units B are adapted to be administered during a second administration interval following the first administration interval, optionally all administration units C are adapted to be administered during a third administration interval following the second administration interval, optionally all administration units D are adapted to be administered during a fourth administration interval following the third administration interval, and optionally all administration units E are adapted to be administered during a fifth administration interval following the fourth administration interval.

Preferably, administration units A, administration units B, optional administration units C, optional administration units D and optional administration units E are each adapted to be administered once daily (sid), twice daily (bid) or thrice daily (tid), twice daily (bid) being particularly preferred.

According to one preferred embodiment of the present invention, the medicament comprises:
(i) a plurality of administration units A as defined supra that are adapted to be administered during a first administration interval of at least 2 days, preferably at least 3 days, preferably twice daily (bid),
(ii) a plurality of administration units B as defined supra that are adapted to be administered during a second administration interval of at least 2 days, preferably at least 3 days, more preferably at least 11 days, following the first administration interval, preferably twice daily (bid),
(iii) optionally, a plurality of administration units C as defined supra that are adapted to be administered during a third administration interval of at least 2 days, preferably at least 3 days, more preferably at least 14 days, following the second administration interval, preferably twice daily (bid),
(iv) optionally, a plurality of administration units D as defined supra that are adapted to be administered during a fourth administration interval of at least 2 days, preferably at least 3 days, following the third administration interval, preferably twice daily (bid), and
(v) optionally, a plurality of administration units E as defined supra that are adapted to be administered during a fifth administration interval of at least 2 days, preferably at least 3 days, following the fourth administration interval, preferably twice daily (bid).

Particularly preferably, the medicament comprises
(i) a plurality of administration units A containing dose a of tapentadol, that are adapted to be orally administered twice daily (bid) during a first administration interval of at least $\alpha$ consecutive days,
(ii) a plurality of administration units B containing dose b of tapentadol, that are adapted to be orally administered twice daily (bid) during a second administration interval of at least $\beta$ consecutive days following the first administration interval,
(iii) optionally, a plurality of administration units C containing dose c of tapentadol, that are adapted to be orally administered twice daily (bid) during a third administration interval of at least $\chi$ consecutive days following the second administration interval,
(iv) optionally, a plurality of administration units D containing dose d of tapentadol, that are adapted to be orally administered twice daily (bid) during a fourth administration interval of at least $\delta$ consecutive days following the third administration interval, and
(v) optionally, a plurality of administration units E containing dose e of tapentadol, that are adapted to be orally administered twice daily (bid) during a fifth administration interval of at least $\epsilon$ consecutive days following the fourth administration interval;

where a, b, c, d, e and $\alpha$, $\beta$, $\chi$, $\delta$, $\epsilon$ satisfy any requirement selected from the group of requirements $P_{1-9}$, $Q_{1-9}$, $R_{1-9}$ and $S_{1-9}$:

| [mg] | d | $P_1$ | $P_2$ | $P_3$ | $P_4$ | $P_5$ | $P_6$ | $P_7$ | $P_8$ | $P_9$ |
|---|---|---|---|---|---|---|---|---|---|---|
| a = 25 ± 5% | $\alpha$ | ≥2 | ≥2 | ≥2 | ≥3 | ≥3 | ≥3 | ≥4 | ≥4 | ≥4 |
| b = 50 ± 5% | $\beta$ | ≥2 | ≥2 | ≥3 | ≥3 | ≥3 | ≥4 | ≥4 | ≥4 | ≥5 |
| C = 100 ± 5% | $\chi$ | ≥2 | ≥3 | ≥3 | ≥3 | ≥4 | ≥4 | ≥4 | ≥5 | ≥5 |
| D = 150 ± 5% | $\delta$ | 0/≥2 | 0/≥3 | 0/≥3 | 0/≥3 | 0/≥4 | 0/≥4 | 0/≥4 | 0/≥5 | 0/≥5 |
| E = 200 ± 5% | $\epsilon$ | 0/≥2 | 0/≥3 | 0/≥3 | 0/≥3 | 0/≥4 | 0/≥4 | 0/≥4 | 0/≥5 | 0/≥5 |

| [mg] | d | $Q_1$ | $Q_2$ | $Q_3$ | $Q_4$ | $Q_5$ | $Q_6$ | $Q_7$ | $Q_8$ | $Q_9$ |
|---|---|---|---|---|---|---|---|---|---|---|
| a = 50 ± 5% | $\alpha$ | ≥2 | ≥2 | ≥3 | ≥3 | ≥4 | ≥4 | ≥5 | ≥5 | ≥6 |
| B = 100 ± 5% | $\beta$ | ≥2 | ≥2 | ≥3 | ≥4 | ≥4 | ≥5 | ≥5 | ≥6 | ≥6 |
| C = 150 ± 5% | $\chi$ | 0/≥2 | 0/≥2 | 0/≥3 | 0/≥4 | 0/≥4 | 0/≥5 | 0/≥5 | 0/≥6 | 0/≥6 |
| D = 200 ± 5% | $\delta$ | 0/≥2 | 0/≥2 | 0/≥3 | 0/≥4 | 0/≥4 | 0/≥5 | 0/≥5 | 0/≥6 | 0/≥6 |
| E = 250 ± 5% | $\epsilon$ | 0/≥2 | 0/≥2 | 0/≥3 | 0/≥4 | 0/≥4 | 0/≥5 | 0/≥5 | 0/≥6 | 0/≥6 |

| [mg] | d | $R_1$ | $R_2$ | $R_3$ | $R_4$ | $R_5$ | $R_6$ | $R_7$ | $R_8$ | $R_9$ |
|---|---|---|---|---|---|---|---|---|---|---|
| a = 50 ± 5% | $\alpha$ | ≥2 | ≥2 | ≥3 | ≥3 | ≥4 | ≥4 | ≥5 | ≥5 | ≥6 |
| B = 100 ± 5% | $\beta$ | ≥2 | ≥3 | ≥3 | ≥4 | ≥4 | ≥5 | ≥5 | ≥6 | ≥6 |
| C = 200 ± 5% | $\chi$ | 0/≥2 | 0/≥3 | 0/≥3 | 0/≥4 | 0/≥4 | 0/≥5 | 0/≥5 | 0/≥6 | 0/≥6 |

| [mg] | d | $S_1$ | $S_2$ | $S_3$ | $S_4$ | $S_5$ | $S_6$ | $S_7$ | $S_8$ | $S_9$ |
|---|---|---|---|---|---|---|---|---|---|---|
| A = 100 ± 5% | $\alpha$ | ≥2 | ≥2 | ≥3 | ≥3 | ≥4 | ≥4 | ≥5 | ≥5 | ≥6 |
| B = 150 ± 5% | $\beta$ | ≥2 | ≥3 | ≥3 | ≥4 | ≥4 | ≥5 | ≥5 | ≥6 | ≥6 |
| C = 200 ± 5% | $\chi$ | 0/≥2 | 0/≥3 | 0/≥3 | 0/≥4 | 0/≥4 | 0/≥5 | 0/≥5 | 0/≥6 | 0/≥6 |
| D = 250 ± 5% | $\delta$ | 0/≥2 | 0/≥3 | 0/≥3 | 0/≥4 | 0/≥4 | 0/≥5 | 0/≥5 | 0/≥6 | 0/≥6 |

In the above tables, e.g., "0/≥2" means that either the respective dose is not administered, i.e. the titration regimen does not encompass this step ("0"), or the respective dose is administered during an administration interval of at least 2 days ("≥2").

Preferably, tapentadol is used in the manufacture of a medicament for the treatment of pain, wherein dose a of tapentadol is administered twice daily (bid) for α days; then dose b of tapentadol is administered twice daily (bid) for β days; then, optionally, dose c of tapentadol is administered twice daily (bid) for χ days; then, optionally, dose d of tapentadol is administered twice daily for δ days; and then, optionally, dose e of tapentadol twice daily for ε days is administered; where a, b, c, d, e and α, β, χ, δ, ε satisfy any requirement selected from the group of the above requirements $P_{1-9}$, $Q_{1-9}$, $R_{1-9}$ and $S_{1-9}$.

The embodiments $P_1$ to $P_9$ are particularly useful for the treatment of chronic pain, especially due to osteoarthritis (hip or knee) or low back pain.

The embodiments $Q_1$ to $Q_9$ are particularly useful for the treatment of chronic pain, especially due to osteoarthritis (hip or knee), low back pain or painful diabetic peripheral neuropathy (DPN).

The embodiments $R_1$ to $R_9$ are particularly useful for the treatment of chronic pain, especially due to osteoarthritis (hip or knee) or low back pain.

The embodiments $S_1$ to $S_9$ are particularly useful for the treatment of chronic pain, especially chronic malignant tumor-related pain.

Preferably, administration unit A, administration unit B, optional administration unit C, optional administration unit D and optional administration unit E and the dosage forms belonging to said administration units, respectively, each
  are adapted to be administered orally; and/or
  are solid and/or compressed and/or film coated; and/or
  release tapentadol from a sustained release matrix; and/or
  contain tapentadol in an amount of from 0.001 to 99.999 wt.-%, more preferably 0.1 to 99.9 wt.-%, still more preferably 1.0 to 99.0 wt.-%, yet more preferably 2.5 to 80 wt.-%, most preferably 5.0 to 50 wt.-% and in particular 7.5 to 40 wt.-%, based on the total weight of the administration unit; and/or
  contain a pharmaceutically acceptable carrier and/or pharmaceutically acceptable excipients; and/or
  have a total weight within the range of from 25 to 2,000 mg, more preferably 50 to 1,800 mg, still more preferably 60 to 1,600 mg, yet more preferably 70 to 1,400 mg, most preferably 80 to 1,200 mg and most preferably 100 to 1,000 mg; and/or
  are selected from the group consisting of tablets, capsules, pellets and granules.

In another preferred embodiment of the medicament according to the invention, dose a, dose b, optional dose c, optional dose d and optional dose e are independently selected so that the mean serum concentration of tapentadol is at least 0.1 ng/ml, more preferably at least 1.0 ng/ml, still more preferably at least 2.0 ng/ml, most preferably at least 5.0 ng/ml and in particular at least 10 ng/ml at any point in time during the administration interval(s), except during an initial phase of up to one, two or three days. More preferably, the mean serum concentration of tapentadol is within the range of from 0.1 to 10,000 ng/ml, more preferably 1.0 to 9,000 ng/ml, still more preferably 2.0 to 8,000 ng/ml, yet more preferably 3.0 to 5,000 ng/ml, most preferably 4.0 to 500 ng/ml and in particular 5.0 to 300 ng/ml at any point in time during the administration interval(s), except during an initial phase of up to one, two or three days.

According to a preferred embodiment of the invention, after administration of the medicament twice daily (bid) for a duration of at least 3 days following the regimen according to the invention, the mean serum concentration of tapentadol is at least 15 ng/ml or at least 20 ng/ml, more preferably at least 25 ng/ml or at least 30 ng/ml, still more preferably at least 35 ng/ml or at least 40 ng/ml, most preferably at least 45 ng/ml or at least 50 ng/ml and particularly at least 55 ng/ml or at least 60 ng/ml. A person skilled in the art knows how to measure the serum concentration of tapentadol and its metabolites. In this context it can be referred to e.g. T. M. Tschentke et al., Drugs of the Future, 2006, 31(12), 1053.

In one preferred embodiment, tapentadol is used in the manufacture of a medicament for the treatment of pain, by administration of which medicament
  after 24 hours during a preceding administration interval of at least 2 days, more preferably at least 3 days, a mean serum concentration of tapentadol of at most 27 ng/ml±75% (±67%, ±50%, ±40%, ±30% or ±20%), more preferably at most 24 ng/ml±75% (±67%, ±50%, ±40%, ±30% or ±20%), still more preferably at most 20 ng/ml±75% (±67%, ±50%, ±40%, ±30% or ±20%) is achieved, and
  after 24 hours during a consecutive administration interval of at least 2 days, more preferably at least 3 days, following said preceding administration interval, a mean serum concentration of tapentadol of at least 27 ng/ml±75% (±67%, ±50%, ±40%, ±30% or ±20%), more preferably at least 30 ng/ml±75% (±67%, ±50%, ±40%, ±30% or ±20%), still more preferably at least 33 ng/ml±75% (±67%, ±50%, ±40%, ±30% or ±20%) is achieved.

In another preferred embodiment, tapentadol is used in the manufacture of a medicament for the treatment of pain, by administration of which medicament
  after 24 hours during a preceding administration interval of at least 2 days, more preferably at least 3 days, a mean serum concentration of tapentadol of at most 45 ng/ml±75% (±67%, ±50%, ±40%, ±30% or ±20%), more preferably at most 41 ng/ml±75% (±67%, ±50%, ±40%, ±30% or ±20%), still more preferably at most 37 ng/ml±75% (±67%, ±50%, ±40%, ±30% or ±20%) is achieved, and
  after 24 hours during a consecutive administration interval of at least 2 days, more preferably at least 3 days, following said preceding administration interval, a mean serum concentration of tapentadol of at least 45 ng/ml±75% (±67%, ±50%, ±40%, ±30% or ±20%), more preferably at least 49 ng/ml±75% (±67%, ±50%, ±40%, ±30% or ±20%), still more preferably at least 53 ng/ml±75% (±67%, ±50%, ±40%, ±30% or ±20%) is achieved.

In still another preferred embodiment, tapentadol is used in the manufacture of a medicament for the treatment of pain, by administration of which medicament
  after 24 hours during a preceding administration interval of at least 2 days, more preferably at least 3 days, a mean serum concentration of tapentadol of at most 62 ng/ml±75% (±67%, ±50%, ±40%, ±30% or ±20%), more preferably at most 60 ng/ml±75% (±67%, ±50%, ±40%, ±30% or ±20%), still more preferably at most 57 ng/ml±75% (±67%, ±50%, ±40%, ±30% or ±20%) is achieved, and
  after 24 hours during a consecutive administration interval of at least 2 days, more preferably at least 3 days, following said preceding administration interval, a mean serum concentration of tapentadol of at least 62 ng/ml±75% (±67%, ±50%, ±40%, ±30% or ±20%), more preferably at least 64 ng/ml±75% (±67%, ±50%, ±40%, ±30% or ±20%), still more preferably at least 67 ng/ml±75% (±67%, ±50%, ±40%, ±30% or ±20%) is achieved.

Usually, about 24 hours are needed to achieve steady state conditions within a given administration interval when increasing (or decreasing) the dose of tapentadol from the dose administered during the preceding administration interval to the dose administered during the consecutive administration interval.

Preferably, tapentadol is used in the manufacture of a medicament for the treatment of pain, wherein
tapentadol is administered, preferably twice daily (bid), during a first administration interval of α days, after 24 hours providing a mean serum concentration $C_\alpha$ of tapentadol;
then tapentadol is administered, preferably twice daily (bid), during a second administration interval of β days following said first administration interval, after 24 hours providing a mean serum concentration $C_\beta$ of tapentadol;
then, optionally, tapentadol is administered, preferably twice daily (bid), during a third administration interval of χ days following said second administration interval, after 24 hours providing a mean serum concentration $C_\chi$ of tapentadol;
then, optionally, tapentadol is administered, preferably twice daily (bid), during a fourth administration interval of δ days following said third administration interval, after 24 hours providing a mean serum concentration $C_\delta$ of tapentadol; and,
then, optionally, tapentadol is administered, preferably twice daily (bid), during a fifth administration interval of ε days following said fourth administration interval, after 24 hours providing a mean serum concentration $C_\varepsilon$ of tapentadol, where α, β, χ, δ, ε and $C_\alpha$, $C_\beta$, $C_\chi$, $C_\delta$, $C_\varepsilon$ satisfy any requirement selected from the group of requirements $T_{1-9}$, $U_{1-9}$, $V_{1-9}$ and $W_{1-9}$:

| [ng/ml] | d | $T_1$ | $T_2$ | $T_3$ | $T_4$ | $T_5$ | $T_6$ | $T_7$ | $T_8$ | $T_9$ |
|---|---|---|---|---|---|---|---|---|---|---|
| $C_\alpha = 9 \pm 75\%$ | α | ≥2 | ≥2 | ≥2 | ≥3 | ≥3 | ≥3 | ≥4 | ≥4 | ≥4 |
| $C_\beta = 18 \pm 75\%$ | β | ≥2 | ≥2 | ≥3 | ≥3 | ≥3 | ≥4 | ≥4 | ≥4 | ≥5 |
| $C_\chi = 35 \pm 75\%$ | χ | ≥2 | ≥3 | ≥3 | ≥3 | ≥4 | ≥4 | ≥4 | ≥5 | ≥5 |
| $C_\delta = 55 \pm 75\%$ | δ | 0/≥2 | 0/≥3 | 0/≥3 | 0/≥3 | 0/≥4 | 0/≥4 | 0/≥4 | 0/≥5 | 0/≥5 |
| $C_\varepsilon = 69 \pm 75\%$ | ε | 0/≥2 | 0/≥3 | 0/≥3 | 0/≥3 | 0/≥4 | 0/≥4 | 0/≥4 | 0/≥5 | 0/≥5 |

| [ng/ml] | d | $U_1$ | $U_2$ | $U_3$ | $U_4$ | $U_5$ | $U_6$ | $U_7$ | $U_8$ | $U_9$ |
|---|---|---|---|---|---|---|---|---|---|---|
| $C_\alpha = 18 \pm 75\%$ | α | ≥2 | ≥2 | ≥3 | ≥3 | ≥4 | ≥4 | ≥5 | ≥5 | ≥6 |
| $C_\beta = 35 \pm 75\%$ | β | ≥2 | ≥2 | ≥3 | ≥4 | ≥4 | ≥5 | ≥5 | ≥6 | ≥6 |
| $C_\chi = 55 \pm 75\%$ | χ | 0/≥2 | 0/≥2 | 0/≥3 | 0/≥4 | 0/≥4 | 0/≥5 | 0/≥5 | 0/≥6 | 0/≥6 |
| $C_\delta = 69 \pm 75\%$ | δ | 0/≥2 | 0/≥2 | 0/≥3 | 0/≥4 | 0/≥4 | 0/≥5 | 0/≥5 | 0/≥6 | 0/≥6 |
| $C_\varepsilon = 90 \pm 75\%$ | ε | 0/≥2 | 0/≥2 | 0/≥3 | 0/≥4 | 0/≥4 | 0/≥5 | 0/≥5 | 0/≥6 | 0/≥6 |

| [ng/ml] | d | $V_1$ | $V_2$ | $V_3$ | $V_4$ | $V_5$ | $V_6$ | $V_7$ | $V_8$ | $V_9$ |
|---|---|---|---|---|---|---|---|---|---|---|
| $C_\alpha = 18 \pm 75\%$ | α | ≥2 | ≥2 | ≥3 | ≥3 | ≥4 | ≥4 | ≥5 | ≥5 | ≥6 |
| $C_\beta = 35 \pm 75\%$ | β | ≥2 | ≥3 | ≥3 | ≥4 | ≥4 | ≥5 | ≥5 | ≥6 | ≥6 |
| $C_\chi = 69 \pm 75\%$ | χ | 0/≥2 | 0/≥3 | 0/≥3 | 0/≥4 | 0/≥4 | 0/≥5 | 0/≥5 | 0/≥6 | 0/≥6 |

| [ng/ml] | d | $W_1$ | $W_2$ | $W_3$ | $W_4$ | $W_5$ | $W_6$ | $W_7$ | $W_8$ | $W_9$ |
|---|---|---|---|---|---|---|---|---|---|---|
| $C_\alpha = 35 \pm 75\%$ | α | ≥2 | ≥2 | ≥3 | ≥3 | ≥4 | ≥4 | ≥5 | ≥5 | ≥6 |
| $C_\beta = 55 \pm 75\%$ | β | ≥2 | ≥3 | ≥3 | ≥4 | ≥4 | ≥5 | ≥5 | ≥6 | ≥6 |
| $C_\chi = 69 \pm 75\%$ | χ | 0/≥2 | 0/≥3 | 0/≥3 | 0/≥4 | 0/≥4 | 0/≥5 | 0/≥5 | 0/≥6 | 0/≥6 |
| $C_\delta = 90 \pm 75\%$ | δ | 0/≥2 | 0/≥3 | 0/≥3 | 0/≥4 | 0/≥4 | 0/≥5 | 0/≥5 | 0/≥6 | 0/≥6 |

In further preferred embodiments, the margins of the serum concentrations $C_\alpha$, $C_\beta$, $C_\chi$, $C_\delta$, $C_\epsilon$ in the above tables, instead of ±75%, are ±67%, more preferably ±50%, still more preferably ±40% or ±35%, most preferably ±30% or ±25% and in particular ±20%, ±15%, ±10% or ±5%.

When, for example, tapentadol is administered during a second administration interval of µ days following a first administration interval, after 24 hours providing a mean serum concentration $C_\beta$ of tapentadol, this means that 24 hours after having initiated the second administration interval, the mean serum concentration has reached the value $C_\beta$. Usually, about 24 hours are needed to achieve steady state conditions within a given administration interval when increasing (or decreasing) the dose of tapentadol from the dose administered during the preceding administration interval to the dose administered during the next administration interval.

Further preferred embodiments of the medicament according to the invention are described in connection with the further aspects of the invention.

Pharmaceutical Excipients

Administration units A and B and the optionally present administration units C, D and E of the medicament according to the invention may each comprise 1 or more dosage forms, which in turn may contain, besides tapentadol, additives and/or auxiliary substances. Suitable additives and/or auxiliary substances in the context of this invention include all those substances known to persons skilled in the art for preparing galenical formulations. The choice of these auxiliary substances and the amounts thereof to be employed depend on whether the administration unit/dosage form is to be administered orally, intravenously, intraperitoneally, intradermally, intramuscularly, intranasally, buccally or locally. Formulations in the form of tablets, chewable tablets, coated tablets, capsules, granules, drops, juices or syrups are suitable for oral administration, and solutions, suspensions, easily reconstitutable dry formulations and sprays are suitable for parenteral, topical and inhalatory administration. Suppositories for use in the rectum are a further possibility. The use in a depot in dissolved form, a carrier film or a patch, optionally with the addition of agents which promote penetration through the skin, are examples of suitable forms for percutaneous administration.

Examples of auxiliary substances and additives for the oral administration units/dosage forms include disintegrating agents, lubricants, binders, fillers, mold release agents, optionally solvents, flavorings, sugars, in particular carrier agents, diluents, dyestuffs, antioxidants etc. For suppositories, inter alia, waxes and fatty acid esters can be used, and for compositions for parental administration carrier substances, preservatives, suspension auxiliaries etc. can be used.

The dosage forms comprise preferably 0.05 wt.-% to 99.5 wt.-% of tapentadol, more preferably 0.1 to 90 wt.-%, still more preferably 0.5 to 80 wt.-%, most preferably 1.0 to 50 wt.-% and in particular 5.0 to 20 wt.-%.

Auxiliary substances can be, for example: water, ethanol, 2-propanol, glycerol, ethylene glycol, propylene glycol, polyethylene glycol, polypropylene glycol, glucose, fructose, lactose, sucrose, dextrose, molasses, starch, modified starch, gelatine, sorbitol, inositol, mannitol, microcrystalline cellulose, methylcellulose, carboxymethyl cellulose, cellulose acetate, shellac, cetyl alcohol, polyvinylpyrrolidone, paraffins, waxes, naturally occurring and synthetic gums, gum acacia, alginates, dextran, saturated and unsaturated fatty acids, stearic acid, magnesium stearate, zinc stearate, glyceryl stearate, sodium lauryl sulfate, edible oils, sesame oil, coconut oil, groundnut oil, soya bean oil, lecithin, sodium lactate, polyoxyethylene and polypropylene fatty acid esters, sorbitan fatty acid esters, sorbic acid, benzoic acid, citric acid, ascorbic acid, tannic acid, sodium chloride, potassium chloride, magnesium chloride, calcium chloride, magnesium oxide, zinc oxide, silicon dioxide, titanium oxide, titanium dioxide, magnesium sulfate, zinc sulfate, calcium sulfate, potash, calcium phosphate, dicalcium phosphate, potassium bromide, potassium iodide, talc, kaolin, pectin, crospovidone, agar and bentonite.

The administration units/dosage forms according to the invention may be controlled release, delayed release, prolonged release/extended release, sustained release, repeataction release, etc. Prolonged release administration units/dosage forms are preferred.

The administration units/dosage forms according to the invention are prepared with the aid of means, devices, methods and processes which are well-known in the prior art of pharmaceutical formulation, such as are described, for example, in "Remington's Pharmaceutical Sciences", ed. A. R. Gennaro, 17th ed., Mack Publishing Company, Easton, Pa. (1985), in particular in part 8, chapter 76 to 93.

Thus, e.g., for a solid formulation, such as a tablet, tapentadol can be granulated with a pharmaceutical carrier, e.g. conventional tablet constituents, such as maize starch, lactose, sucrose, sorbitol, talc, magnesium stearate, dicalcium phosphate or pharmaceutically acceptable gums, and pharmaceutical diluents, such as e.g. water, in order to form a solid composition which comprises tapentadol in homogeneous distribution. Homogeneous distribution is understood here as meaning that tapentadol is uniformly distributed over the entire composition, so that this can easily be divided into unit dose forms, such as tablets, pills or capsules, having the same activity. The solid composition is then divided into unit dose forms. The administration units according to the invention can also be coated or compounded in another manner in order to provide a dose form with delayed release. Suitable coating compositions are, inter alia, polymeric acids and mixtures of polymeric acids with materials such as e.g. shellac, cetyl alcohol and/or cellulose acetate.

Tapentadol can be released in a delayed or prolonged or sustained manner from administration units/dosage forms which can be used orally, rectally or percutaneously. Corresponding formulations, in particular in the form of a "twice daily (bid)" preparation which has to be taken only twice a day (bid), are particularly preferred for the indication according to the invention (cf. US-A-2005-58706).

Delayed or prolonged or sustained release of tapentadol may be achieved by administration units/dosage forms which contain tapentadol in a matrix, which contains e.g. 1 to 80% by weight, in particular 5 to 80 by weight, of one or more hydrophilic or hydrophobic polymers as pharmaceutically acceptable matrix forming agents and which comprise cellulose ethers and/or cellulose esters having a viscosity (determined using a Pharm. Eu. capillary viscosimeter) of 3,000 to 150,000 mPa s in a 2% by weight aqueous solution at 20° C. as pharmaceutically acceptable matrix forming agents. Preferred pharmaceutically acceptable matrix forming agents include polyethylene oxide having a molecular mass of more than 0.5 mio g/mol, cellulose ethers and/or cellulose esters having a viscosity between 10,000, in particular 50,000 mPa s, and 150,000 mPa s in a 2% by weight aqueous solution at 20° C. Particularly suitable pharmaceutically acceptable matrix forming agents may be selected from the group consisting of hydroxypropylmethyl celluloses (HPMC), hydroxyethyl celluloses, hydroxypropyl celluloses (HPC), methyl celluloses, ethyl celluloses and carboxymethyl celluloses and are selected, in particular, from the group consisting of HPMCs, hydroxyethyl celluloses and HPCs. HPMCs having a viscosity of approximately 100,000 mPa s, measured in a 2% by weight aqueous solution at 20° C. are most preferred.

The administration units/dosage forms according to the invention can exist both as a simple tablet and as a coated tablet, for example as a film tablet or dragee. The tablets are typically round and biconvex, but oblong tablet shapes which allow the tablet to be divided are also possible. Granules, spheroids, pellets or microcapsules which are poured into sachets or capsules or may be compressed to disintegrating tablets are also possible within the scope of the invention.

Instead of a slow release matrix, it is also possible to use a normal release matrix with a coating which retards release of the active ingredient. For example, tapentadol can be contained in a conventional matrix of microcrystalline cellulose and optionally further pharmaceutical auxiliaries such as binders, fillers, glidants, lubricants and flow regulators, which are covered or coated with a material controlling the slow release of tapentadol in an aqueous medium. Suitable coating agents include, for example, water-insoluble waxes and polymers such as polymethacrylates (Eudragit or the like) or water-insoluble celluloses, in particular ethyl cellulose. The coating material can optionally also contain water-soluble polymers such as polyvinyl pyrrolidone, water-soluble celluloses such as hydroxypropylmethyl cellulose or hydroxypropyl cellulose, other water-soluble agents such as Polysorbate 80 or hydrophilic pore-forming agents such as polyethylene glycol, lactose or mannitol.

As an alternative or a supplement to the possibilities of a slow release matrix in the delayed release or prolonged release or sustained release dosage forms or of a normal release matrix with a coating which retards the release of tapentadol, an osmotically driven release system can also be used to achieve a slow release. Embodiments and examples of the actual production of osmotically driven release systems can be found in U.S. Pat. Nos. 4,765,989, 4,783,337, and 4,612,008.

Kit

A further aspect of the invention relates to a kit comprising at least one administration unit A, at least one administration unit B, optionally at least one administration unit C, optionally at least one administration unit D and optionally at least one administration unit E, as defined above. The kit according to the invention preferably comprises a packaging containing a plurality of administration units A each comprising $n_A$ dosage forms, a plurality of administration units B each comprising $n_B$ dosage forms, optionally a plurality of administration units C each comprising $n_C$ dosage forms, optionally a plurality of administration units D each comprising $n_D$ dosage forms, and optionally a plurality of administration units E each comprising $n_D$ dosage forms, where $n_A$, $n_B$, optional $n_C$, optional $n_D$ and optional $n_E$ are preferably independently of one another 1, 2, 3, 4 or 5.

Figure 3:
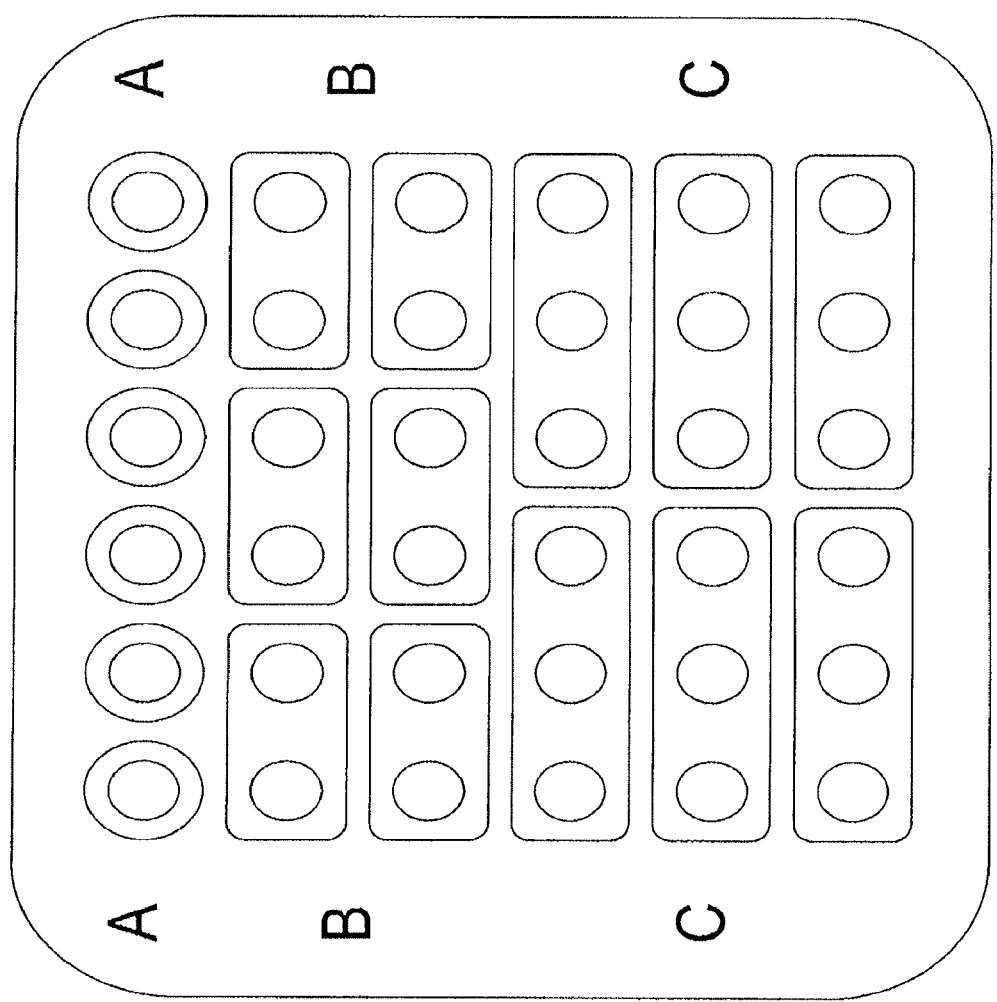

Preferably, the $n_X$ dosage form(s) belonging to a particular administration unit X are grouped and/or marked and/or locally separated from the other administration units and dosage forms, respectively, that are contained in the packaging (cf. FIGS. 2 and 3).

In one preferred embodiment, all dosage forms contained in the kit according to the invention are identical, i.e. contain the same amount of tapentadol, and $n_A < n_B <$ optional $n_C <$ optional $n_D <$ optional $n_E$, more preferably $n_A=1$, $n_B=2$, optional $n_C=3$, optional $n_D=4$, and optional $n_E=5$. Preferably, dose $a/n_A$=dose $b/n_B$=optional dose $c/n_C$=optional dose $d/n_D$=optional dose $e/n_E$.

In another preferred embodiment, the dosage forms that belong to administration unit(s) A differ from the dosage forms that belong to administration unit(s) B, which in turn differ from the dosage forms that belong to administration unit(s) C, and so on. Preferably, $n_A=n_B$=optional $n_C$=optional $n_D$=optional $n_E=1$ or 2 (cf. FIG. 4).

Preferably, the kit according to the invention comprises a plurality of administration units and dosage forms, respectively, suitable for administering dose a of tapentadol twice daily (bid) for α days, then dose b of tapentadol twice daily (bid) for β days, then optionally dose c of tapentadol twice daily (bid) for x days, then optionally dose d of tapentadol twice daily for δ days, and then optionally dose e of tapentadol twice daily for ε days, where a, b, c, d, e and α, β, χ, δ, ε satisfy any requirement selected from the group of the above requirements $P_{1-9}$, $Q_{1-9}$, $R_{1-9}$ and $S_{1-9}$.

Further preferred embodiments of the kit according to the invention are described in connection with the further aspects of the invention.

Dosage Form Having a Predetermined Site of Fracture

Still another aspect of the invention relates to a pharmaceutical oral dosage form containing tapentadol, which comprises a notch that divides the dosage form into at least two portions and mechanically weakens the dosage form so that it may be manually broken at the notch along a predetermined site of fracture (breaking notch). The dosage form is preferably adapted to be administered twice daily (bid) and tapentadol is embedded in a retard matrix. The matrix ensures that delayed release of tapentadol from the dosage form is not diminished when breaking the administration unit at the notch. The notch may be linear or assume the shape of a cross. When the notch is linear, the dosage form may be broken into two halves, which preferably have about the same shape, size and content of tapentadol. When the notch assumes the shape of a cross, the dosage form may be broken into two halves and each have in turn may be broken into two quarts, which preferably have about the same shape, size and content of tapentadol. Preferably, the dosage form contains 40 to 260 mg of tapentadol. Preferably, after being broken at the notch along the predetermined site of fracture, each halve contains about 20 to about 130 mg of tapentadol and each quart contains about 10 to about 65 mg of tapentadol respectively.

The dosage form according to the invention may be used to realize a titration regimen. For example, if tapentadol is to be administered twice daily (bid) during the first administration interval at a dose of 100 mg±5% and during the second administration interval at a dose of 200 mg±5%, the dosage form according to the invention may contain a total of 200 mg±5% of tapentadol. For administration during the first administration interval, each dosage form is manually broken and only a halve containing about 100 mg±5% of tapentadol is administered. After the first administration interval, the dosage form is not broken anymore, but administered as such.

The individual fragments of the dosage form according to the invention that are obtained when the dosage form is broken along the notch preferably each contain a dose of tapentadol that corresponds to any of doses a, doses b, doses c, doses d, and doses e, respectively, as defined supra.

Method of Treating Pain

A further aspect of the invention relates to a method of treating pain which comprises administering to one in need thereof tapentadol according to a titration regimen, preferably by means of the medicament according to the invention. Preferably, in the regimen tapentadol is administered once daily (sid), twice daily (bid), or thrice daily (tid), twice daily (bid) being particularly preferred.

As far as the doses are concerned, each regimen may be divided into a titration phase and a continuous phase. For the purpose of the specification "titration" means that after a certain administration interval, the dose of tapentadol is increased (or decreased) until the optimal dose is reached.

The regimen may be static (forced) or dynamic. Preferably, the regimen is dynamic, i.e. the dose is successively increased until the optimal, pharmaceutically effective dose for the individual subject has been reached. The optimal dose may vary individually and also depends upon the type and degree of pain to be treated. Preferably, the optimal dose is defined as the dose providing a meaningful improvement of pain with acceptable side effects in the patient's perception (maximum therapeutic benefit). The regimen results in a lower incidence or severity of side effects, such as somnolence.

Preferably, the subject monitors the achievement of amelioration of pain and the occurrence of side effects caused by the current dose of tapentadol. Depending upon the assessment of the desired pain reduction on the one hand and the adverse events on the other hand, the subject decides whether the dose of tapentadol is
further increased (next titration step upwards),
maintained at the current level (no further titration step) or decreased (next titration step downwards).

Preferably, during the titration phase tapentadol is administered twice daily (bid) at a constant first (initial) dose for a first administration interval. After said first administration interval, tapentadol is administered twice daily (bid) at a constant second dose for a second administration interval, with the proviso that the second dose is higher than the first dose.

After said second administration interval, the titration phase may be terminated, i.e. administration of tapentadol may be continued twice daily (bid) at said constant second dose, thereby initiating the continuous phase. Under these circumstances, the titration phase is terminated by the fact that the dose of tapentadol that was administered during the second administration interval is no further increased (or decreased). Alternatively, after said second administration interval, the titration phase may continue, i.e. tapentadol is administered twice daily (bid) at a constant third dose for a third administration interval, with the proviso that the third dose is higher than the second dose.

After said third administration interval, the titration phase may be terminated, i.e. administration of tapentadol may be continued twice daily (bid) at said constant third dose, thereby initiating the continuous phase. Alternatively, after said third administration interval, the titration phase may continue, i.e. tapentadol is administered twice daily (bid) at a constant fourth dose for a fourth administration interval. At this stage the dose may be either further increased or decreased, depending on the individual needs of the subject.

Preferably, the titration phase encompasses at least 2 administration intervals, preferably 3, 4 or 5 administration intervals, at which different doses of tapentadol are administered, preferably twice daily (bid), resulting in biphasic, triphasic, tetraphasic and pentaphasic regimens, respectively.

Preferably, the titration phase of the dosing regimen comprises at least 1, 2, 3, 4, 5, 6 or 7 days, more preferably at least 14 days, still more preferably 7 to 28 days, most preferably 14 to 28 days and in particular 14 to 21 days.

In one preferred embodiment, the dosing regimen is biphasic (two consecutive administration intervals), comprises 1, 2, 3, 4, 5, 6 or 7 to 28 days, more preferably 7 to 21 days and most preferably 7 to 14 days, the dose of tapentadol at the first administration interval is within the range of from 50 mg±5% to 100 mg±5%, preferably twice daily (bid), and the dose of tapentadol at the second administration interval is within the range of from 100 mg±5% to 150 mg±5%, preferably twice daily (bid). Preferably, the second administration interval commences 2 to 11, more preferably 3 to 7 days after initiation of administration of tapentadol.

In another preferred embodiment, the dosing regimen is triphasic (three consecutive administration intervals), comprises 1, 2, 3, 4, 5, 6 or 7 to 28 days, more preferably 7 to 21 days and most preferably 7 to 14 days, the dose of tapentadol at the first administration interval is within the range of from 25 mg±5% to 100 mg±5%, preferably twice daily (bid), the dose of tapentadol at the second administration interval is within the range of from 50 mg±5% to 150 mg±5%, preferably twice daily (bid), and the dose of tapentadol at the third administration interval is within the range of from 100 mg±5% to 200 mg±5%, preferably twice daily (bid). Preferably, the second administration interval commences 2 to 11, more preferably 3 to 7 days after initiation of administration of tapentadol and the third administration interval commences 5 to 22, more preferably 6 to 14 days after initiation of administration of tapentadol.

In still another preferred embodiment, the dosing regimen is tetraphasic (four consecutive administration intervals), comprises 1, 2, 3, 4, 5, 6 or 7 to 28 days, more preferably 7 to 21 days and most preferably 14 to 21 days, the dose of tapentadol at the first administration interval is within the range of from 25 mg±5% to 100 mg±5%, preferably twice daily (bid), the dose of tapentadol at the second administration interval is within the range of from 50 mg±5% to 150 mg±5%, preferably twice daily (bid), the dose of tapentadol at the third administration interval is within the range of from 100 mg±5% to 200 mg±5%, preferably twice daily (bid), and the dose of tapentadol at the fourth administration interval is within the range of from 150 mg±5% to 250 mg±5%, preferably twice daily (bid). Preferably, the second administration interval commences 2 to 11, more preferably 3 to 7 days after initiation of administration of tapentadol, the third administration interval commences 5 to 16, more preferably 6 to 14 days after initiation of administration of tapentadol and the fourth administration interval commences 8 to 22, more preferably 9 to 14 days after initiation of administration of tapentadol.

In yet another preferred embodiment, the dosing regimen is pentaphasic (five consecutive administration intervals), comprises 1, 2, 3, 4, 5, 6 or 7 to 28 days, more preferably 7 to 21 days and most preferably 14 to 21 days, the dose of tapentadol at the first administration interval is within the range of from 25 mg±5% to 50 mg±5%, preferably twice daily (bid), the dose of tapentadol at the second administration interval is within the range of from 50 mg±5% to 100 mg±5%, preferably twice daily (bid), the dose of tapentadol at the third administration interval is within the range of from 100 mg±5% to 150 mg±5%, preferably twice daily (bid), the dose of tapentadol at the fourth administration interval is within the range of from 150 mg±5% to 200 mg±5%, preferably twice daily (bid), and the dose of tapentadol at the fifth administration interval is within the range of from 200 mg±5% to 250 mg±5%, preferably twice daily (bid). Preferably, the second administration interval commences 2 to 11, more preferably 3 to 7 days after initiation of administration of tapentadol, the third administration interval commences 5 to 16, more preferably 6 to 14 days after initiation of administration of tapentadol, the fourth administration interval commences 8 to 22, more preferably 9 to 14 days after initiation of administration of tapentadol, and the fifth administration interval commences 11 to 27, more preferably 12 to 17 days after initiation of administration of tapentadol.

The individual doses that are to be administered may be administered by a single administration unit containing the entire dose or by a plurality of administration units each containing a portion of said entire dose. For example, a dose of 100 mg tapentadol may be administered either by a tablet containing 100 mg or by two tablets each containing 50 mg.

The method for treating pain, preferably of chronic pain, according to the invention follows a titration regimen. Preferably, the method comprises administering to one in need thereof dose a of tapentadol, preferably once daily (sid), twice daily (bid) or thrice daily (tid), during a first administration interval and dose b of tapentadol, preferably once daily (sid), twice daily (bid) or thrice daily (tid), during a second administration interval following the first administration interval, where dose a<dose b.

Preferably, the first administration interval and the second administration interval last independently of one another at least 1 day, more preferably at least 2 days and in particular at least 3 days.

Preferably, tapentadol is administered orally. Preferably, tapentadol is administered twice daily (bid). Preferably, dose a is within the range of from 10 to 90 wt.-% of dose b, more preferably from 20 to 80 wt.-%, still more preferably from 45 to 70 wt.-%.

In one preferred embodiment, the method according to the invention further comprises orally administering dose c of tapentadol once daily (sid), twice daily (bid) or thrice daily (tid) during a third administration interval following the second administration interval, where dose b<dose c. Preferably, dose a is within the range of from 10 to 65 wt.-% of dose c, more preferably from 20 to 55 wt.-%, and dose b is within the range of from 35 to 90 wt.-% of dose c, more preferably from 45 to 80 wt.-%.

In a further preferred embodiment, the method according to the invention further comprises orally administering dose d of tapentadol once daily (sid), twice daily (bid) or thrice daily (tid) during a fourth administration interval following the third administration interval, where dose c<dose d (or where dose c>dose d). Preferably, dose a is within the range of from 10 to 55 wt.-% of dose d, more preferably 15 to 50 wt.-%, dose b is within the range of from 35 to 75 wt.-% of dose d, more preferably 40 to 70 wt.-%, and dose c is within the range of from 60 to 95 wt.-% of dose d, more preferably 65 to 90 wt.-%.

In a still further preferred embodiment, the method according to the invention further comprises orally administering dose e of tapentadol once daily (sid), twice daily (bid) or thrice daily (tid) during a fifth administration interval following the fourth administration interval, where dose d<dose e (where dose d>dose e). Preferably, dose a is within the range of from 10 to 30 wt.-% of dose e, more preferably 15 to 25 wt.-%, dose b is within the range of from 30 to 50 wt.-% of dose e, more preferably 35 to 45 wt.-%, dose c is within the range of from 50 to 70 wt.-% of dose e, more preferably 55 to 65 wt.-%, and dose d is within the range of from 70 to 90 wt.-% of dose e, more preferably 75 to 85 wt.-%.

Preferably, the first administration interval, second administration interval, optional third administration interval, optional fourth administration interval and optional fifth administration interval comprise independently of one another 1 to 21 days, more preferably 2 to 14 days.

Preferably, the method according to the invention comprises administering (i) dose a of tapentadol once daily (sid), twice daily (bid) or thrice daily (tid) during a first administration interval of at least 2 days, preferably at least 3 days, (ii) dose b of tapentadol once daily (sid), twice daily (bid) or thrice daily (tid) during a second administration interval of at least 2 days, preferably at least 3 days, following the first administration interval, (iii) optionally, dose c of tapentadol once daily (sid), twice daily (bid) or thrice daily (tid) during a third administration interval of at least 2 days, preferably at least 3 days, following the second administration interval, (iv) optionally, dose d of tapentadol once daily (sid), twice daily (bid) or thrice daily (tid) during a fourth administration interval of at least 2 days, preferably at least 3 days, following the third administration interval, and (v) optionally, dose e of tapentadol once daily (sid), twice daily (bid) or thrice daily (tid) during a fifth administration interval of at least 2 days, preferably at least 3 days, following the fourth administration interval.

Preferably, the number of administrations per day is harmonized, i.e. when during the first administration interval tapentadol is administered twice daily (bid), during the second administration interval tapentadol is preferably also administered twice daily (bid), i.e. neither once daily (sid) nor thrice daily (tid).

In one preferred embodiment of the method according to the invention, dose a, dose b, optional dose c, optional dose d and optional dose e are independently selected so that the daily dose of tapentadol on every day of every administration interval is within the range of from 20 to 550 mg, more preferably 30 to 530 mg and most preferably 40 to 510 mg.

Particularly preferably, the method according to the invention comprises orally administering (i) dose a of tapentadol twice daily (bid) during a first administration interval of at least $\alpha$ consecutive days, (ii) dose b of tapentadol twice daily (bid) during a second administration interval of at least $\beta$ consecutive days following the first administration interval, (iii) optionally, dose c of tapentadol twice daily (bid) during a third administration interval of at least $\chi$ consecutive days following the second administration interval, (iv) optionally, dose d of tapentadol twice daily (bid) during a fourth administration interval of at least $\delta$ consecutive days following the third administration interval, and (v) optionally, dose e of tapentadol twice daily (bid) during a fifth administration interval of at least $\varepsilon$ consecutive days following the fourth administration interval;

where a, b, c, d, e and $\alpha$, $\beta$, $\chi$, $\delta$, $\varepsilon$ satisfy any requirement selected from the group of requirements $P_{1-9}$, $Q_{1-9}$, $R_{1-9}$ and $S_{1-9}$ as described supra.

In a particularly preferred embodiment, subjects initiate treatment with tapentadol, orally administered twice daily (bid), at a dose of 50 mg±5%. After 3 days the dose is increased to 100 mg±5%. This is the minimum dose to be continued with. To the discretion of the subject, upward titration may then occur at a minimum of 3-day intervals (6 consecutive doses) in increments of 50 mg±5%. The maximum dose allowed is preferably 250 mg±5%. To the discretion of the subject, downward titration (preferably not below the minimum dose) is also permitted using the same decrements without a time restriction.

In still another particularly preferred embodiment subjects initiate treatment with tapentadol, orally administered twice daily (bid), at a dose of 50 mg±5%. After 3 days the dose is increased to 100 mg±5%. This is the minimum dose to be continued with. The subject remains on the 100 mg±5% dose for the next 4 days. Thereafter, to the discretion of the subject, upward titration may occur at a minimum of 3-day intervals (6 consecutive doses) in increments of 50 mg±5%. The maximum dose allowed is preferably 250 mg±5%. To the discretion of the subject, downward titration (preferably not below the minimum dose) is also permitted using the same decrements without a time restriction.

The two foregoing embodiments are particularly useful for the treatment of chronic pain, especially due to osteoarthritis (hip or knee), low back pain, painful diabetic peripheral neuropathy (DPN) and malignant pain.

In another particularly preferred embodiment subjects initiate treatment with tapentadol, orally administered twice daily (bid), at a dose of 100 mg±5%. This is the minimum dose to be continued with. To the discretion of the subject, upward titration may then occur at a minimum of 3-day intervals (6 consecutive doses) in increments of 50 mg±5%. The maximum dose allowed is preferably 250 mg±5%. To the discretion of the subject, downward titration (preferably not below the minimum dose) is also permitted using the same decrements without a time restriction. This embodiment is particularly useful for the treatment of chronic pain, especially chronic malignant tumor-related pain.

Preferably, the usual initial dose is 50 mg of tapentadol prolonged release (PR) twice daily (bid). Patients are individually titrated to the optimal individual dose, which is defined as the dose providing a meaningful improvement of pain with acceptable side effects in the patient's perception (maximum therapeutic benefit). Upward titration may occur at intervals in increments of 50 mg tapentadol prolonged release (PR) twice daily (bid). Downward titration should use the same decrements. The dose used should be the lowest dose that provides pain relief. Tapentadol may be administered with or without food.

Preferably, the usual initial dose is 50 mg of tapentadol prolonged release (PR) twice daily (bid). Patients are individually titrated to the optimal individual dose, which is defined as the dose providing a meaningful improvement of pain with acceptable side effects in the patient's perception (maximum therapeutic benefit). Upward titration may occur at a minimum of 3-day intervals (6 consecutive doses) in increments of 50 mg tapentadol prolonged release (PR) twice daily (bid). Downward titration using the same decrements can be performed without a time restriction. The dose used should be the lowest dose that provides pain relief. The maximum dose is 250 mg tapentadol prolonged release (PR) twice daily (bid). Tapentadol may be administered with or without food.

In another preferred embodiment of the method according to the invention, dose a, dose b, optional dose c, optional dose d and optional dose e are independently selected so that the mean serum concentration of tapentadol is within the range of from 0.1 to 10,000 ng/ml, more preferably 1.0 to 9,000 ng/ml, still more preferably 2.0 to 8,000 ng/ml, most preferably 3.0 to 1,000 ng/ml and in particular 5.0 to 300 ng/ml at any point in time, except the initial phase of one, two or three days.

In a preferred embodiment of the method according to the invention, tapentadol is administered, preferably twice daily (bid), during a first administration interval of $\alpha$ days, after 24 hours providing a mean serum concentration $C_\alpha$ of tapentadol;

then tapentadol is administered, preferably twice daily (bid), during a second administration interval of $\beta$ days following said first administration interval, after 24 hours providing a mean serum concentration $C_\beta$ of tapentadol;

then, optionally, tapentadol is administered, preferably twice daily (bid), during a third administration interval of $\chi$ days following said second administration interval, after 24 hours providing a mean serum concentration $C_\chi$ of tapentadol;

then, optionally, tapentadol is administered, preferably twice daily (bid), during a fourth administration interval of 8 days following said third administration interval, after 24 hours providing a mean serum concentration $C_\delta$ of tapentadol; and, then, optionally, tapentadol is administered, preferably twice daily (bid), during a fifth administration interval of $\varepsilon$ days following said fourth administration interval, after 24 hours providing a mean serum concentration $C_a$ of tapentadol, where $\alpha$, $\beta$, $\chi$, $\delta$, $\varepsilon$ and $C_\alpha$, $C_\beta$, $C_\chi$, $C_\delta$, $C_\varepsilon$ satisfy any requirement selected from the group of requirements $T_{1-9}$, $U_{1-9}$, $V_{1-9}$ and $W_{1-9}$:

| [ng/ml] | d | $T_1$ | $T_2$ | $T_3$ | $T_4$ | $T_5$ | $T_6$ | $T_7$ | $T_8$ | $T_9$ |
|---|---|---|---|---|---|---|---|---|---|---|
| $C_\alpha = 9 \pm 75\%$ | $\alpha$ | ≥2 | ≥2 | ≥2 | ≥3 | ≥3 | ≥3 | ≥4 | ≥4 | ≥4 |
| $C_\beta = 18 \pm 75\%$ | $\beta$ | ≥2 | ≥2 | ≥3 | ≥3 | ≥3 | ≥4 | ≥4 | ≥4 | ≥5 |
| $C_\chi = 35 \pm 75\%$ | $\chi$ | ≥2 | ≥3 | ≥3 | ≥3 | ≥4 | ≥4 | ≥4 | ≥5 | ≥5 |
| $C_\delta = 55 \pm 75\%$ | $\delta$ | 0/≥2 | 0/≥3 | 0/≥3 | 0/≥3 | 0/≥4 | 0/≥4 | 0/≥4 | 0/≥5 | 0/≥5 |
| $C_\varepsilon = 69 \pm 75\%$ | $\varepsilon$ | 0/≥2 | 0/≥3 | 0/≥3 | 0/≥3 | 0/≥4 | 0/≥4 | 0/≥4 | 0/≥5 | 0/≥5 |

| [ng/ml] | d | $U_1$ | $U_2$ | $U_3$ | $U_4$ | $U_5$ | $U_6$ | $U_7$ | $U_8$ | $U_9$ |
|---|---|---|---|---|---|---|---|---|---|---|
| $C_\alpha = 18 \pm 75\%$ | $\alpha$ | ≥2 | ≥2 | ≥3 | ≥3 | ≥4 | ≥4 | ≥5 | ≥5 | ≥6 |
| $C_\beta = 35 \pm 75\%$ | $\beta$ | ≥2 | ≥2 | ≥3 | ≥4 | ≥4 | ≥5 | ≥5 | ≥6 | ≥6 |
| $C_\chi = 55 \pm 75\%$ | $\chi$ | 0/≥2 | 0/≥2 | 0/≥3 | 0/≥4 | 0/≥4 | 0/≥5 | 0/≥5 | 0/≥6 | 0/≥6 |
| $C_\delta = 69 \pm 75\%$ | $\delta$ | 0/≥2 | 0/≥2 | 0/≥3 | 0/≥4 | 0/≥4 | 0/≥5 | 0/≥5 | 0/≥6 | 0/≥6 |
| $C_\varepsilon = 90 \pm 75\%$ | $\varepsilon$ | 0/≥2 | 0/≥2 | 0/≥3 | 0/≥4 | 0/≥4 | 0/≥5 | 0/≥5 | 0/≥6 | 0/≥6 |

| [ng/ml] | d | $V_1$ | $V_2$ | $V_3$ | $V_4$ | $V_5$ | $V_6$ | $V_7$ | $V_8$ | $V_9$ |
|---|---|---|---|---|---|---|---|---|---|---|
| $C_\alpha = 18 \pm 75\%$ | α | ≥2 | ≥2 | ≥3 | ≥3 | ≥4 | ≥4 | ≥5 | ≥5 | ≥6 |
| $C_\beta = 35 \pm 75\%$ | β | ≥2 | ≥3 | ≥3 | ≥4 | ≥4 | ≥5 | ≥5 | ≥6 | ≥6 |
| $C_\chi = 69 \pm 75\%$ | χ | 0/≥2 | 0/≥3 | 0/≥3 | 0/≥4 | 0/≥4 | 0/≥5 | 0/≥5 | 0/≥6 | 0/≥6 |

| [ng/ml] | d | $W_1$ | $W_2$ | $W_3$ | $W_4$ | $W_5$ | $W_6$ | $W_7$ | $W_6$ | $W_9$ |
|---|---|---|---|---|---|---|---|---|---|---|
| $C_\alpha = 35 \pm 75\%$ | α | ≥2 | ≥2 | ≥3 | ≥3 | ≥4 | ≥4 | ≥5 | ≥5 | ≥6 |
| $C_\beta = 55 \pm 75\%$ | β | ≥2 | ≥3 | ≥3 | ≥4 | ≥4 | ≥5 | ≥5 | ≥6 | ≥6 |
| $C_\chi = 69 \pm 75\%$ | χ | 0/≥2 | 0/≥3 | 0/≥3 | 0/≥4 | 0/≥4 | 0/≥5 | 0/≥5 | 0/≥6 | 0/≥6 |
| $C_\delta = 90 \pm 75\%$ | δ | 0/≥2 | 0/≥3 | 0/≥3 | 0/≥4 | 0/≥4 | 0/≥5 | 0/≥5 | 0/≥6 | 0/≥6 |

In further preferred embodiments, the margins of the serum concentrations $C_\alpha$, $C_\beta$, $C_\chi$, $C_\delta$, $C_\epsilon$ in the above tables, instead of ±75%, are ±67%, more preferably ±50%, still more preferably ±40% or ±35%, most preferably ±30% or ±25% and in particular ±20%, ±15%, ±10% or ±5%. Usually, about 24 hours are needed to achieve steady state conditions within a given administration interval when increasing (or decreasing) the dose of tapentadol from the dose administered during the preceding administration interval to the dose administered during the next administration interval.

As already mentioned above, the overall dosing regimen typically comprises a titration phase followed by a continuous phase. In a preferred embodiment, the overall dosing regimen (titration phase+continuous phase) includes at least 10 consecutive days, more preferably at least 20 consecutive days, still more preferably at least 30 consecutive days, yet more preferably at least 50 consecutive days, most preferably at least 70 consecutive days and in particular at least 90 consecutive days.

In one preferred embodiment the overall administration is terminated after the titration phase and the subsequent continuous phase have been completed, i.e., after the continuous phase preferably no second titration phase (e.g., downward titration, drug tapering) is supplemented. In other words, at the end of the overall dosing regimen the administration of tapentadol is preferably terminated at once, i.e. from the full dose (last regular dose) at the continuous phase down to zero without any intermediate doses.

It has been surprisingly found that for tapentadol at the end of a long term dosing regimen, the occurrence of mild-moderate withdrawal symptoms following drug discontinuation are significantly fewer compared to other opioids, such as oxycodone. Thus, there is little indication of the need for drug tapering (downward titration) at the end of the overall dosing regimen.

Further preferred embodiments of the method according to the invention are described in connection with the further aspects of the invention.

The titration of tapentadol is effective in reducing discontinuations due to adverse effects while maintaining the analgesic properties of the compound. This is particularly true in the case of patients who previously had difficulty tolerating an analgesic because of side effects such as somnolence. This result is based on the cumulative proportion of patients who discontinued use of the agent due to adverse side effects.

EXAMPLES

The following examples describe the invention in greater detail and are intended to illustrate the invention but not to limit its scope.

A) Comparative Example C-1 (without Titration)

Design:
A randomized, double-blind, multiple dose, parallel-group study assessing the efficacy and safety of 3 dosages of tapentadol prolonged release (bid) (25 mg, 50 mg and 100 mg) compared to oxycodone prolonged release (bid) 20 mg and placebo over 28 days in patients with hip and/or knee-joint osteoarthritis.
Subjects:
40-75 years old, male and female patients.
375 patients, randomized to placebo, standard opioid, tapentadol.
Treatment Regimen:
Day 1 only evening dose
Day 2—Day 28 bid
Day 29 only morning dose.

B) Comparative Example C-2 (without Titration)

Design:
A randomized, double-blind, multiple dose, parallel-group study assessing the efficacy and safety of tapentadol prolonged release 25, 50 and 100 mg compared to placebo and tramadol prolonged release 100 mg in patients with chronic low back pain.
Subjects:
Male and female patients 18-75 years old with a history of low back pain of at least 6 months, requiring regular treatment on at least 60 out of last 90 days.
430 patients, randomized to placebo, tramadol 100 mg prolonged release, 3 dosages tapentadol.
Treatment Regimen:
Daily bid for 28 days C) Example E-1 (Forced Titration—Static Regimen)

Design:
A randomized, double-blind, parallel-group study assessing the efficacy and safety of two titration regimen of tapentadol prolonged release (25 mg, 50 mg, 100 mg and 100 mg, 150 mg, 200 mg of free base of tapentadol) given orally twice daily (bid) compared to placebo and oxycodone controlled release (10 mg, 10 mg, 20 mg) in patients with chronic pain due to osteoarthritis of the knee.
Subjects:
Male and female patients≥40 years old with a diagnosis of osteoarthritis of the knee
Treatment Regimen:
Patients started with the lowest dose of the titration phase for the first 3 days and up-titrated to the intermediate dose on day 4. Subjects were maintained at the intermediate dose for the next 11 days. After these 11 days patients started the maintenance phase and received the highest dose of each regimen for the remaining 14 days. Subjects who were unable to tolerate the highest dose after having received that dose for at least 3 days were allowed to down titrate to the intermediate dose. Down titration was permitted only once during the fixed-dose maintenance phase.

D) Example E-2 (Forced Titration—Static Regimen)

Design:
A randomized, double-blind, parallel-group study that compares the efficacy and safety of two titration regimens of tapentadol prolonged release (25 mg-50 mg-100 mg and 100 mg-150 mg-200 mg) given orally twice daily (bid) and tramadol prolonged release (100 mg-150 mg-200 mg) p.o. bid to placebo in patients with moderate to severe chronic pain due to chronic low back pain.
Subjects:
Male and female patients≥18 years old with a diagnosis of low back pain of at least 3 months.
Treatment Regimen:
Patients took the first dose and continued on the lowest dose in their treatment regimen for 3 days (i.e. 6 doses). After the sixth dose, patients titrated to the intermediate dose in their treatment regimen and continued on this intermediate dose for 11 days (i.e. 22 doses). Up-titration was mandatory. Patients who were unable to tolerate study medication were removed from the study. After the twenty second dose, patients titrated to the final dose in their treatment regimen and continued on this final dose for 14 days.
E) Using Modeling & Simulation (M&S) to estimate the influence of dose titration with tapentadol on the occurrence of somnolence.

PK/PD modeling and simulation were used to investigate if dose titration would bring a benefit for the development of adverse events. The estimation of advantage of dose titration was based on somnolence as an indicator for typical opioid related adverse events. It was also one of the adverse events most commonly occurring and therefore enabling a modeling and simulation with enough reliability.

Concentration measurements were taken from comparative examples C-1 and C-2, both without dose titration. Examples E-1 and E-2 in the same indications were used to get PK/PD information under dose titration. In all studies adverse events were noted.

Figure 5:
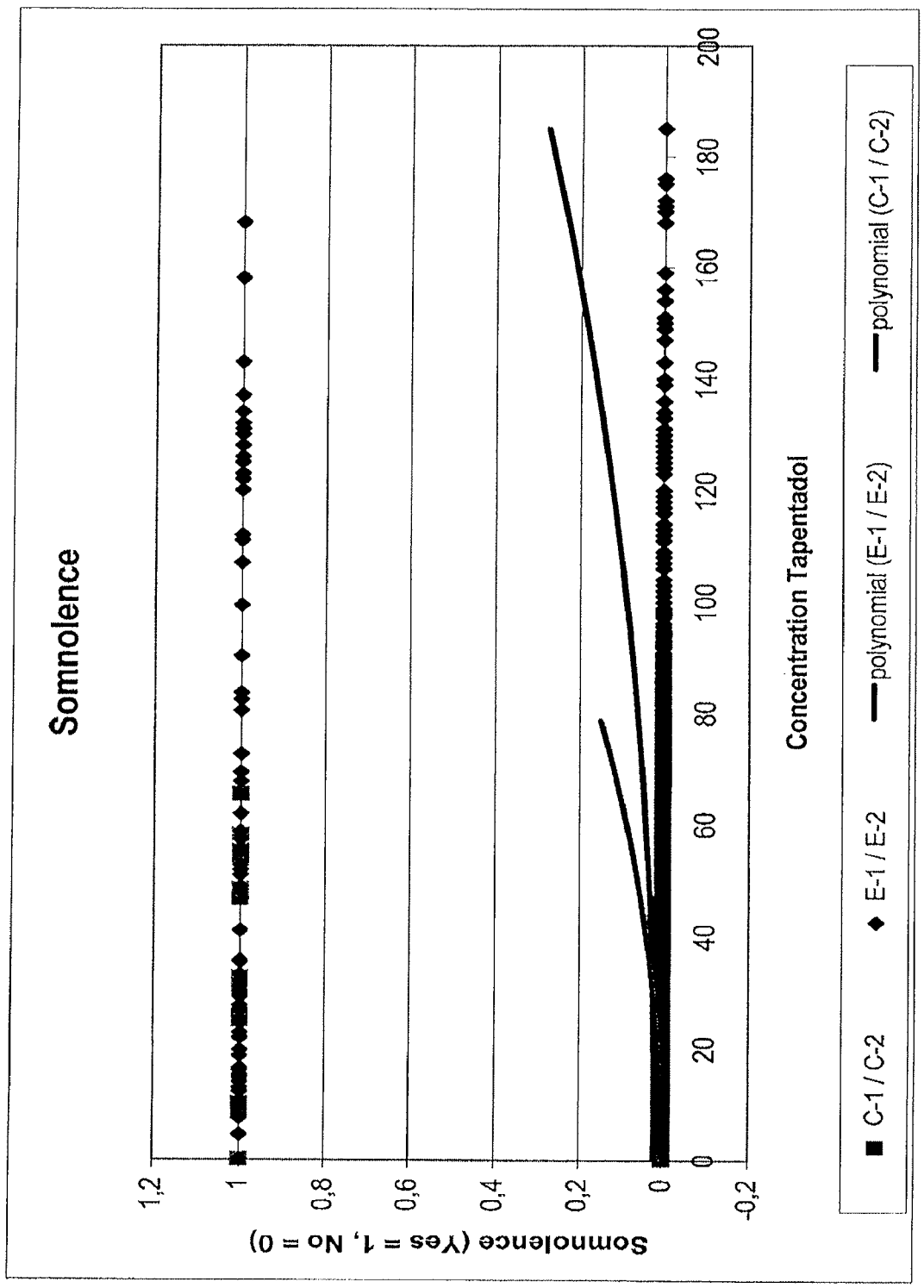
FIGS. 5 and 6 show the effect of titration of tapentadol prolonged release (PR) on the occurrence of somnolence observed in clinical trials (examples E-1 and E-2 vs. comparative examples C-1 and C-2).

A population PK model was build over all studies using NONMEM V level 1.1 and a population PK/PD model was build for somnolence for studies of examples E-1 and E-2. Simulations were performed using Trial Simulator 2.1, taking into account the PK/PD model for somnolence established for the data from the studies of examples E-1 and E-2 and the population PK model without covariates for all 4 studies.
Results PK/PD Somnolence:
FIG. 5 (Tapentadol—observations of somnolence versus concentration with a 2 degree polynomial fitting) and FIG. 6 (Tapentadol—observations of somnolence versus concentration with a 6 degree polynomial fitting) clearly show that despite the dosages and concentrations being clearly lower in the studies of comparative examples C-1 and C-2, adverse events occurred typically at a much lower concentration compared to the studies of examples E-1 and E-2 in which dose titration was used.

Figure 6:
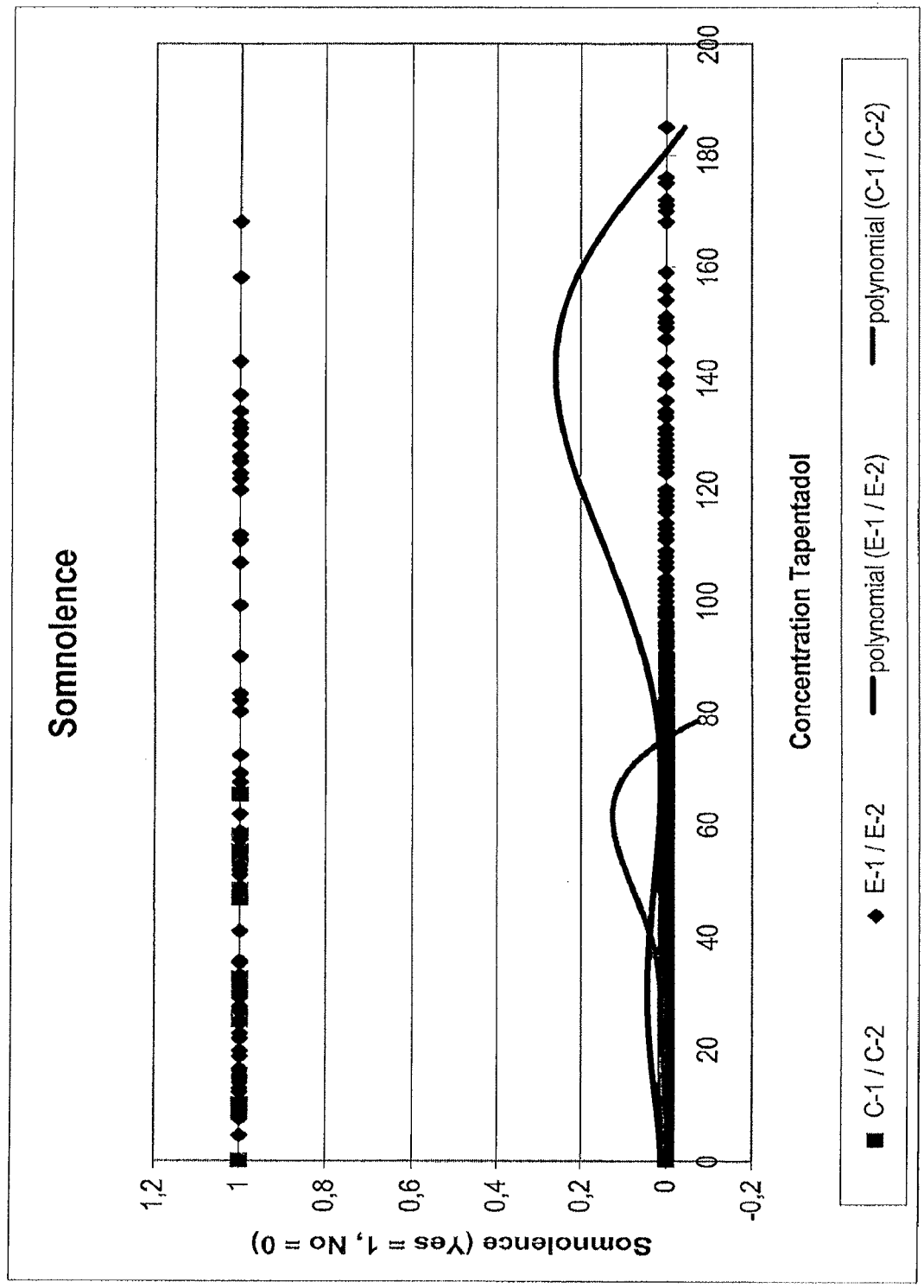

From FIG. 6 it can be seen that in the range of concentrations where enough somnolence was present the curves for the studies with and without dose titration run almost in parallel but shifted to lower concentrations if no titration was applied. The downward bend at the end of the polynomial regression is caused by a lack of high concentrations, a phenomenon normally seen with a high degree polynomial.

Due to the similarity of the curves and the lower number of data points in the studies of comparative examples C-1 and C-2 no model was build for this PK/PD relationship. Instead, the numbers found for examples E1 and E2 were adapted so the results of simulating the comparative examples C-1 and C-2 would resemble the curve in FIGS. 5 and 6.

The following equations, obtained by modeling was used to establish the probability for somnolence for the dose titration:

$$\text{Log it}=-3.4+0.000445 \ast \text{Concentration}^{1.74}$$

For fixed dose the following equation was derived from the equation above based on FIGS. 5 and 6:

$$\text{Log it}=-3.4+0.0009 \ast \text{Concentration}^{1.74}$$

Figure 7:
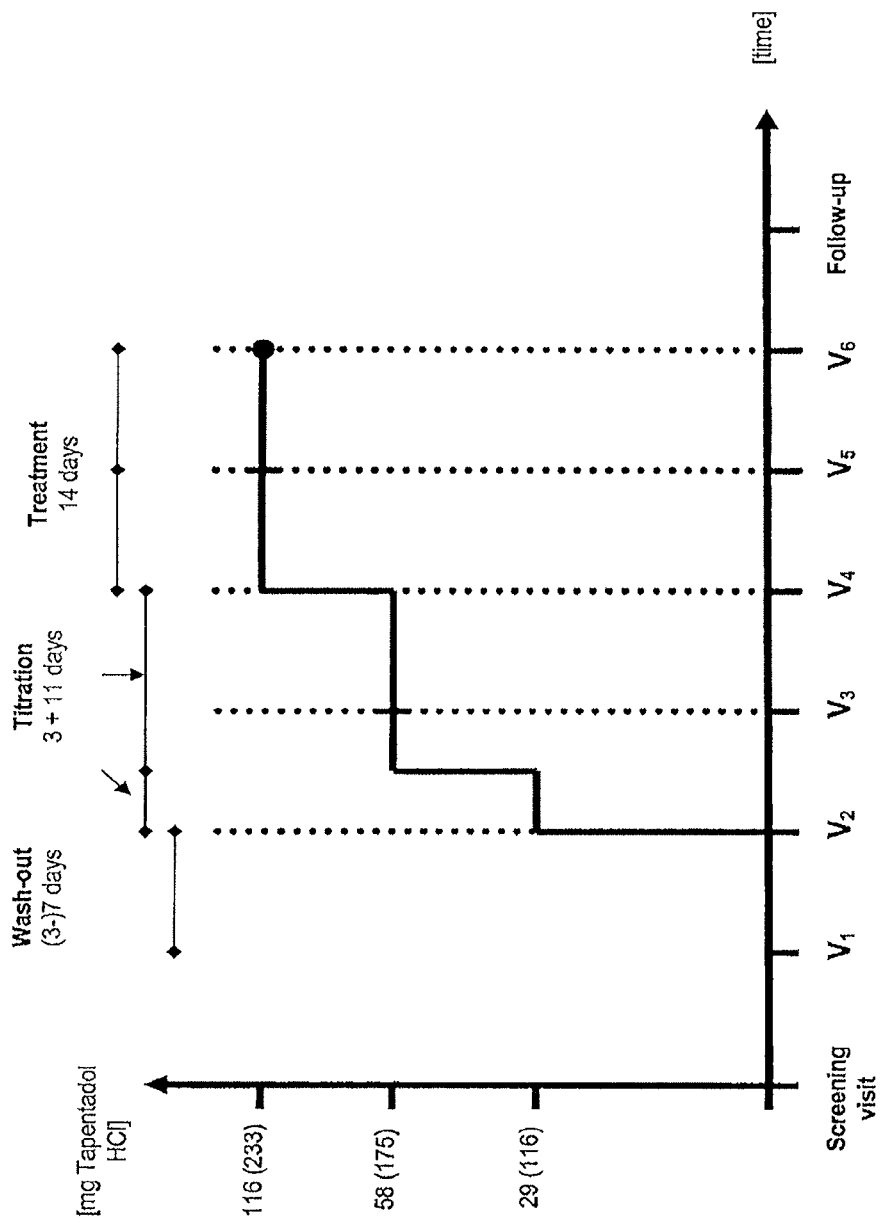
FIG. 7 schematically illustrates a preferred titration regimen for tapentadol prolonged release (PR).

FIG. 7 shows a schematic illustration of the titration regimen used for tapentadol in the clinical studies.
Results PK/PD Simulations:
The population PK model together with the relationship between concentrations and somnolence was used to simulate 2000 patients, 1000 patients with dose titration (1 week 58 mg, 1 week 116 mg, 2 weeks 233 mg tapentadol HCl) and 1000 patients without dose titration (4 weeks at 233 mg). It was simulated what the probability in both designs would be when the subject was asked whether he had somnolence three times a day for seven days during the $4^{th}$ week of treatment. Drop outs were not taken into account in the simulation procedures.

Result clearly indicate that the number of somnolence episodes was much lower in the group that was having dose titration. Overall the number of somnolence episodes in the last week of treatment was 15.5% in the group with dose titration versus 33.2% in the group with fixed dose. Mean of the concentrations on each of the times the question for somnolence was asked reached were almost identical in the two dose groups. When just looking at the last concentration at the last visit the incidence of somnolence was 7.6% in the dose titration group versus 12.9% in the fixed dose group.

In the studies which did not use titration somnolence occurred in 4.3% of patients at a total daily dose of 172 mg tapentadol base (pooled data from both studies). However, in the studies using forced titration somnolence occurred in 6% of patients at a total daily dose of 200 mg, and in 12% of patients at a total daily dose of 400 mg tapentadol base (pooled data).

F) Comparison—Titration of Oxycodone

Figure 8:
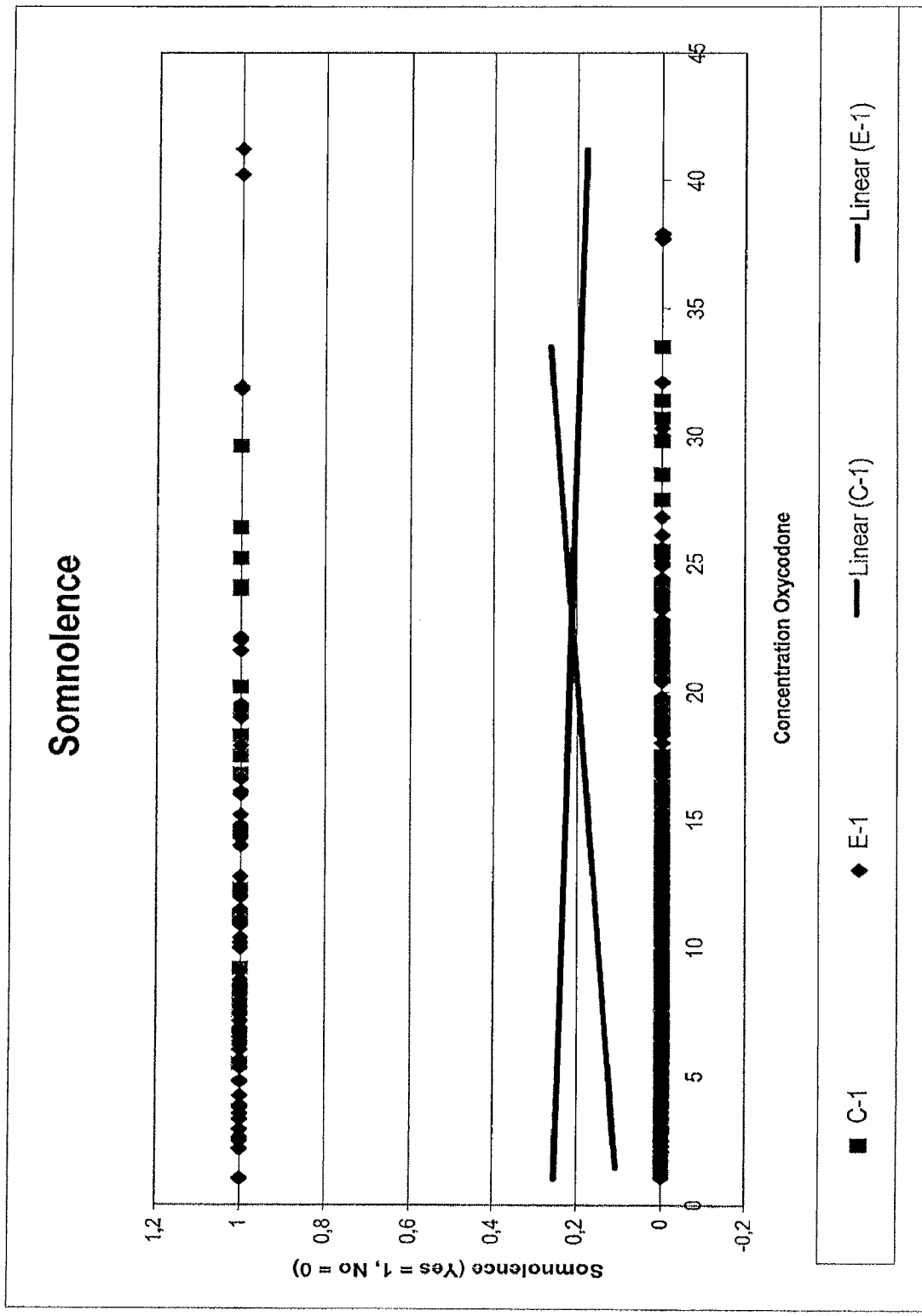
FIG. 8 shows the effect of titration of oxycodone controlled release (CR) on the occurrence of somnolence observed in clinical trials (example E-1 vs. comparative example C-1).

FIG. 8 (oxycodone—observations of somnolence versus concentration with a linear fitting) indicates that when administering oxycodone according to the titration regimen of example E-1, there is no comparable effect on the suppression of somnolence.

G) Serum Concentrations of Tapentadol

Figure 9:
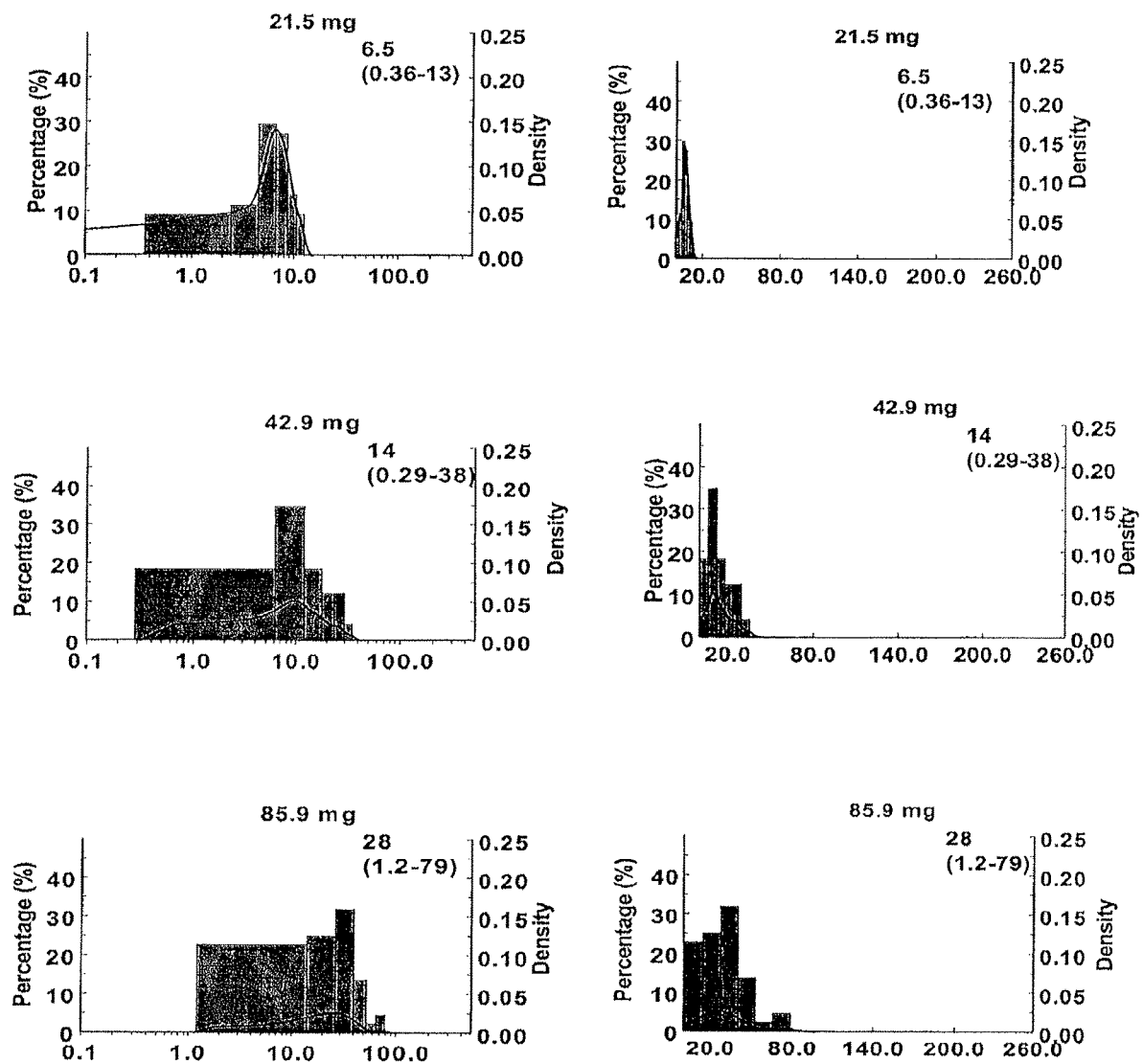
FIGS. 9 A/B show a mathematical analysis of the distribution of serum concentrations of tapentadol (ng/ml) after administration in comparative clinical trials (comparative examples C-1 and C-2).
Figure 9:
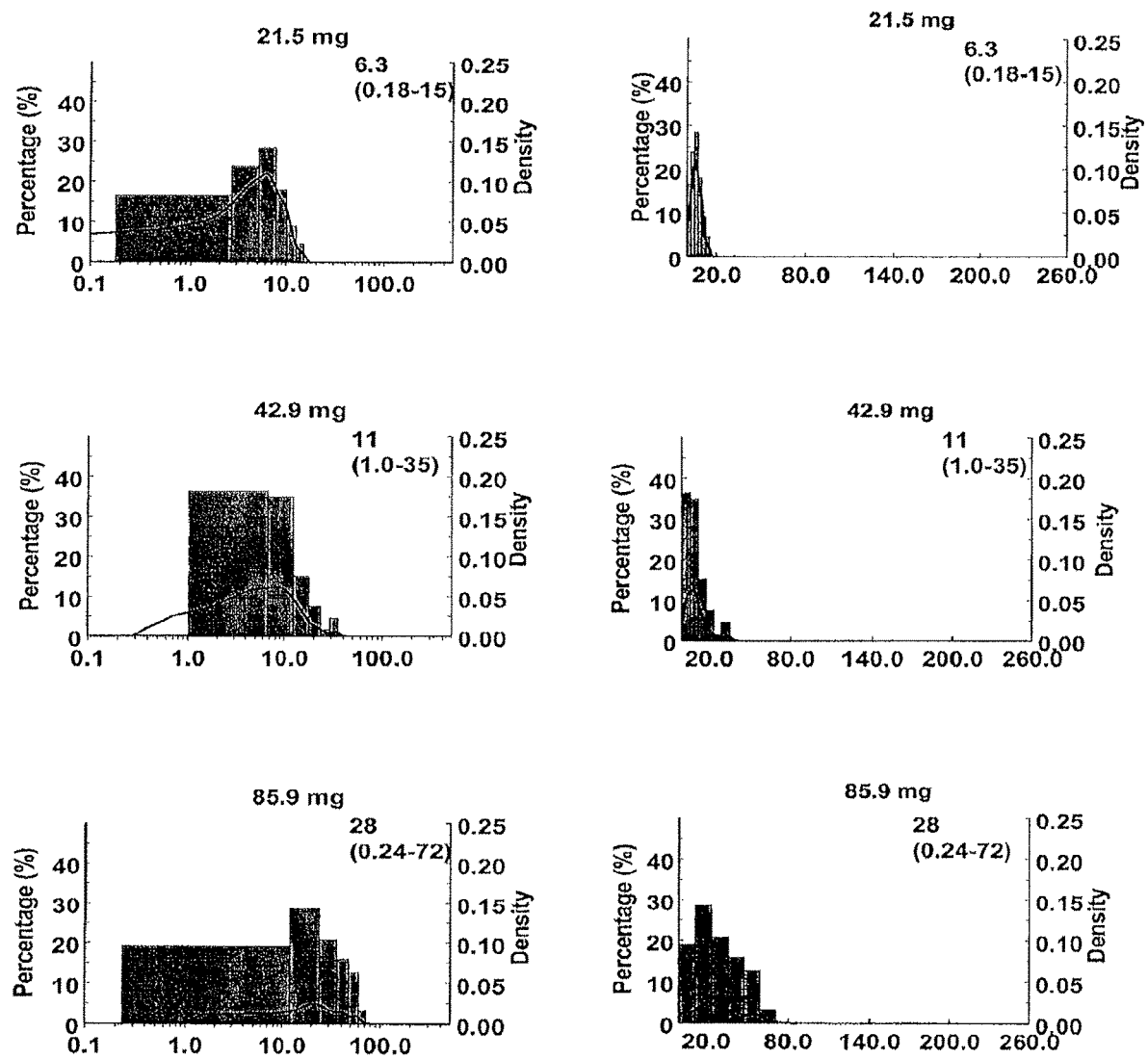

FIGS. 9 A/B show a mathematical analysis of the distribution of concentrations of tapentadol (ng/ml) after administration in the comparative clinical trials (comparative examples C-1 and C-2).

Figure 10:
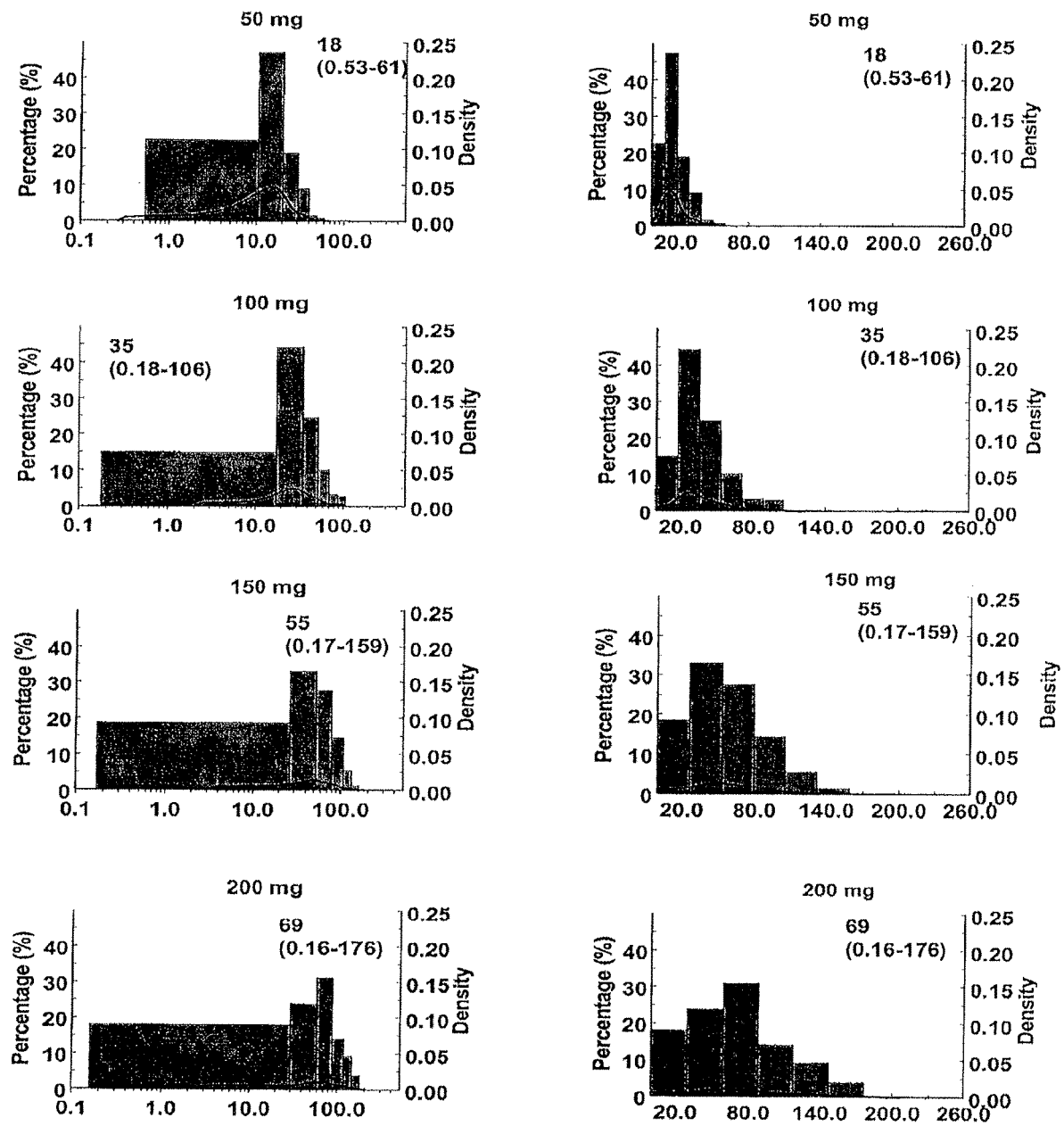
FIGS. 10 A/B show a mathematical analysis of the distribution of serum concentrations of tapentadol (ng/ml) after administration in the clinical trials according to the invention (examples E-1 and E-2).
Figure 10:
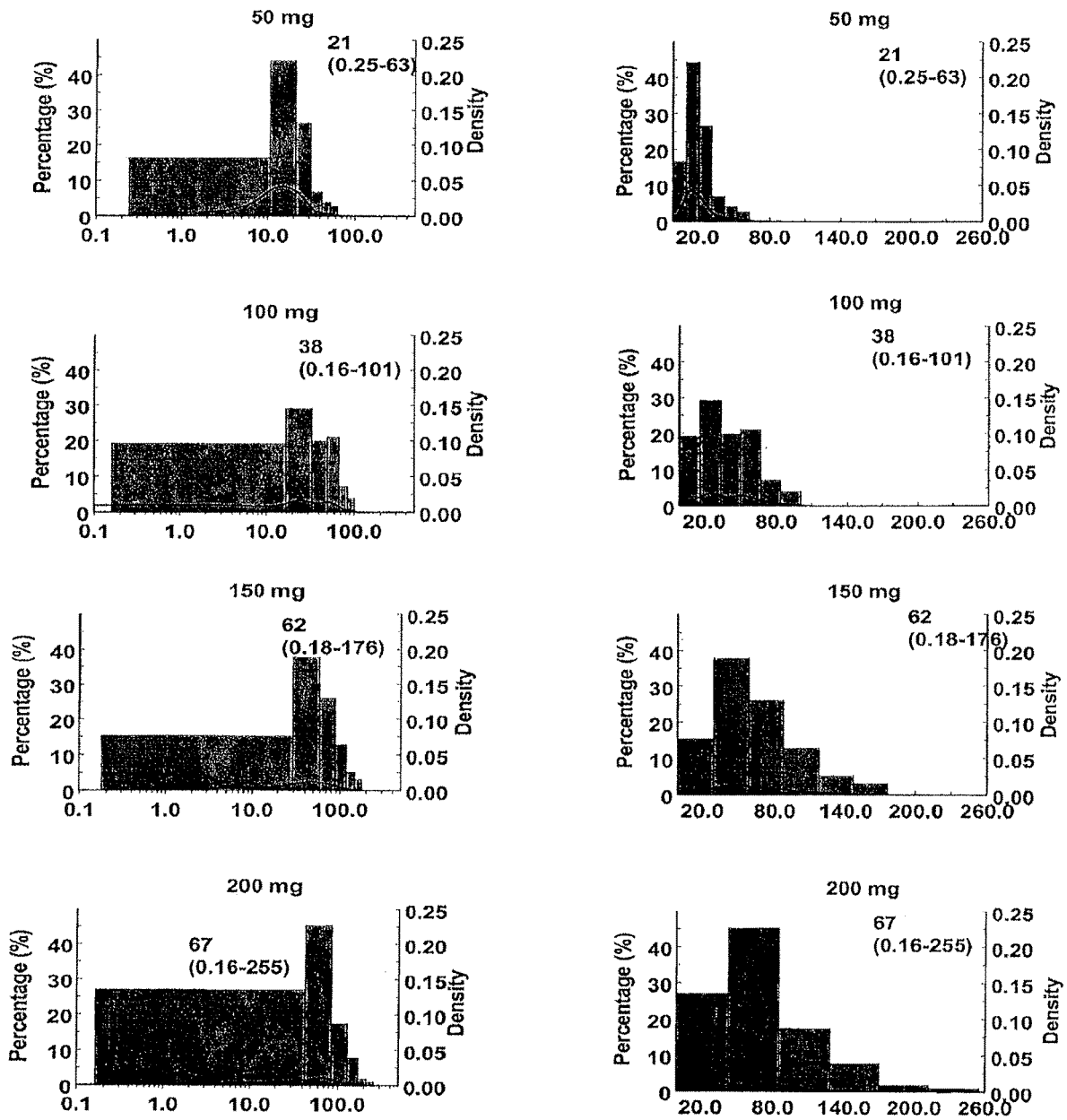

FIGS. 10 A/B show a mathematical analysis of the distribution of concentrations of tapentadol (ng/ml) after administration in the clinical trials according to the invention (examples E-1 and E-2).

H) Example E-3 (End of Administration Regimen)

The symptoms of opioid withdrawal following long-term treatment (90 days) with tapentadol immediate release (IR) compared with oxycodone IR were evaluated in a randomized, double-blind, active-control, parallel group, flexible dose, multicenter phase III trial of patients with chronic low back pain of chronic pain from osteoarthritis of the knee or hip. Patients (N=849) were randomly assigned in a 4:1 ratio to a flexible dose of tapentadol IR (50 or 100 mg/dose; maximum 600 mg/day) or oxycodone IR (10 or 15 mg/dose; maximum 90 mg/day) every 4 to 6 hours. Symptoms of withdrawal following opioid discontinuation were examined using the Clinical Opioid Withdrawal Score (COWS) and the Subjective Opioid Withdrawal Score (SOWS) questionnaires. Based on the COWS assessment 2 to 4 days after study medication ceased, patients reporting mild-to-moderate withdrawal symptoms were significantly less in the tapentadol IR group (17%) than the oxycodone IR group (29%; nominal P<0.05 using Cochran-Mantel-Haenszel test). The mean total SOWS score, 2 to 4 days after last study drug intake, was lower for the tapentadol IR group (6.9) than the oxycodone IR group (8.7). The corresponding P value (analysis of variance model) revealed no significant difference between the treatment groups. In addition, 5 or more days after last study drug intake, the mean total SOWS score was 6.3 for the tapentadol IR group and 7.0 for the oxycodone IR group (no significant difference). These findings suggest that although there is a possibility of withdrawal, there is little indication of the need for drug tapering.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed is:

1. A method of treating pain with a lower incidence of somnolence in a subject in need thereof, said method comprising orally administering to said subject:
   (i) a first dose of tapentadol of 50 mg±5% or 100 mg±5% twice daily (bid) during a first administration interval of at least 1-3 days;
   (ii) a second dose of tapentadol calculated by increasing said first dose by 50 mg to 100 mg±5% or 150 mg±5% twice daily (bid), respectively, during a second administration interval of at least 3-11 days following said first administration interval; and
   (iii) a third dose of tapentadol calculated by increasing said second dose by 50 mg to 150 mg±5% or 200 mg±5% twice daily (bid), respectively, during a third administration interval of at least 3-14 days following said second administration interval.

2. The method according to claim 1, which comprises orally administering to said subject:
   (i) a first dose of tapentadol of 50 mg±5% twice daily (bid) during the first administration interval of at least 1-3 days;
   (ii) a second dose of tapentadol of 100 mg±5% twice daily (bid) during the second administration interval of at least 3-11 days following said first administration interval; and
   (iii) a third dose of tapentadol of 150 mg±5% twice daily (bid) during the third administration interval of at least 3-14 days following said second administration interval.

3. The method according to claim 1, which comprises orally administering to said subject:
   (i) a first dose of tapentadol of 100 mg±5% twice daily (bid) during the first administration interval of at least 1-3 days;
   (ii) a second dose of tapentadol of 150 mg±5% twice daily (bid) during the second administration interval of at least 3-11 days following said first administration interval; and
   (iii) a third dose of tapentadol of 200 mg±5% twice daily (bid) during the third administration interval of at least 3-14 days following said second administration interval.

* * * * *